(12) United States Patent
King et al.

(10) Patent No.: US 7,987,845 B2
(45) Date of Patent: Aug. 2, 2011

(54) DRY POWDER INHALERS HAVING SPIRAL TRAVEL PATHS, UNIT DOSE MICROCARTRIDGES WITH DRY POWDER, RELATED DEVICES AND METHODS

(75) Inventors: Michael King, Durham, NC (US); Jeffrey Alan Warden, Raleigh, NC (US); John Kim, Chelsea (CA); Benjamin Finney, Cary, NC (US); Nicholas Oxley, New York, NY (US)

(73) Assignee: Oriel Therapeutics, Inc., Durham, NC (US)

( * ) Notice: Subject to any disclaimer, the term of this patent is extended or adjusted under 35 U.S.C. 154(b) by 1197 days.

(21) Appl. No.: 11/625,855

(22) Filed: Jan. 23, 2007

(65) Prior Publication Data

US 2007/0215149 A1 Sep. 20, 2007

Related U.S. Application Data

(60) Provisional application No. 60/763,717, filed on Jan. 31, 2006.

(51) Int. Cl.
*A61M 16/00* (2006.01)
*B65D 83/04* (2006.01)
*B67D 7/06* (2010.01)

(52) U.S. Cl. ......... 128/203.15; 128/203.12; 128/203.21; 128/203.23; 128/205.21; 128/207.14; 221/30; 221/31; 221/42; 221/92; 221/93; 222/80; 222/81; 222/138; 222/141

(58) Field of Classification Search ............. 128/203.15, 128/203.12, 203.21, 203.23, 205.21, 207.14; 221/30, 31, 42, 64, 92, 93, 197, 277; 222/80, 222/81, 138, 141
See application file for complete search history.

(56) References Cited

U.S. PATENT DOCUMENTS

| | | | |
|---|---|---|---|
| 3,410,450 A * | 11/1968 | Fortenberry | ..................... 221/7 |
| 3,948,264 A | 4/1976 | Wilke et al. | |
| 4,013,075 A | 3/1977 | Cocozza | |
| 5,048,514 A | 9/1991 | Ramella | |
| 5,415,162 A * | 5/1995 | Casper et al. | ............ 128/203.12 |

(Continued)

FOREIGN PATENT DOCUMENTS

EP 9469814 A1 2/1992

(Continued)

OTHER PUBLICATIONS

Crowder et al. "2001: An Odyssey in Inhaler Formulation and Design" *Pharmaceutical Technology* 25(7):99-113 (2001).

(Continued)

*Primary Examiner* — Justine R Yu
*Assistant Examiner* — Clinton Ostrup
(74) *Attorney, Agent, or Firm* — Myers Bigel Sibley & Sajovec, P.A.

(57) ABSTRACT

Dry powder inhalers include: (a) a first generally planar spiral travel path in an inhaler body, wherein the first spiral travel path has a plurality of adjacent curvilinear channels forming lanes with upstanding sidewalls, including an inner lane and an outer lane; and (b) a plurality of discrete sealed microcartridges with substantially rigid bodies disposed in the first travel path, each comprising a pre-metered (typically dose) amount of dry powder, the microcartridges being configured to slidably advance along the first travel path toward an inhalation chamber that merges into an inhalation output port. In operation, at least one microcartridge is held in the inhalation chamber to release the dry powder therein during inhalation.

24 Claims, 23 Drawing Sheets

U.S. PATENT DOCUMENTS

| | | | |
|---|---|---|---|
| 5,533,502 | A | 7/1996 | Piper |
| 5,560,490 | A | 10/1996 | Chawla |
| 5,562,918 | A | 10/1996 | Stimpson |
| 5,595,175 | A | 1/1997 | Malcher et al. |
| 5,655,523 | A | 8/1997 | Hodson et al. |
| 5,673,686 | A | 10/1997 | Villax et al. |
| 5,685,294 | A | 11/1997 | Gupte et al. |
| 5,687,710 | A | 11/1997 | Ambrosio et al. |
| 5,718,355 | A | 2/1998 | Garby et al. |
| 5,727,607 | A | 3/1998 | Ichikawa et al. |
| 5,740,793 | A | 4/1998 | Hodson et al. |
| 5,769,073 | A | 6/1998 | Eason et al. |
| 5,787,881 | A | 8/1998 | Chawla |
| 5,881,721 | A | 3/1999 | Bunce et al. |
| 5,909,829 | A | 6/1999 | Wegman et al. |
| 5,924,417 | A * | 7/1999 | Braithwaite ............. 128/203.15 |
| 5,947,169 | A | 9/1999 | Wegman et al. |
| 5,983,893 | A | 11/1999 | Wetterlin |
| 6,029,663 | A | 2/2000 | Eisele et al. |
| 6,415,790 | B1 | 7/2002 | Leedom et al. |
| 6,470,884 | B2 | 10/2002 | Hörlin |
| 6,488,027 | B1 | 12/2002 | Moulin |
| 6,520,179 | B1 | 2/2003 | Von Schuckmann et al. |
| 6,526,969 | B2 | 3/2003 | Hilsson et al. |
| 6,553,987 | B1 | 4/2003 | Davies |
| 6,592,930 | B2 | 7/2003 | Nilsson |
| 6,626,173 | B2 * | 9/2003 | Genova et al. ............ 128/203.15 |
| 6,655,381 | B2 | 12/2003 | Keane et al. |
| 6,679,255 | B2 | 1/2004 | Pera |
| 6,748,947 | B2 | 6/2004 | Keane et al. |
| 6,752,148 | B1 | 6/2004 | McGinn et al. |
| 6,772,755 | B2 | 8/2004 | Pera |
| 6,840,239 | B2 | 1/2005 | Myrman |
| 6,871,646 | B2 | 3/2005 | Keane et al. |
| 6,880,722 | B2 | 4/2005 | Anderson et al. |
| 6,889,690 | B2 | 5/2005 | Crowder et al. |
| 6,948,496 | B2 | 9/2005 | Eason et al. |
| 6,971,383 | B2 | 12/2005 | Hickey et al. |
| 7,025,056 | B2 | 4/2006 | Eason et al. |
| 7,025,057 | B2 | 4/2006 | Chawla |
| 7,025,059 | B2 | 4/2006 | Pera |
| 7,151,456 | B2 | 12/2006 | Godfrey |
| 7,171,965 | B2 | 2/2007 | Young et al. |
| 7,178,518 | B2 | 2/2007 | Watt et al. |
| 7,219,665 | B1 * | 5/2007 | Braithwaite ............. 128/203.21 |
| 7,249,600 | B2 | 7/2007 | Chawla |
| 2001/0007853 | A1 | 7/2001 | Dimarchi et al. |
| 2001/0020472 | A1 | 9/2001 | Horlin |
| 2001/0053761 | A1 | 12/2001 | Dimarchi et al. |
| 2002/0162552 | A1 | 11/2002 | Pera |
| 2003/0015195 | A1 | 1/2003 | Haaije de Boer et al. |
| 2003/0056789 | A1 | 3/2003 | Takano et al. |
| 2003/0140923 | A1 | 7/2003 | Taylor et al. |
| 2004/0025876 | A1 | 2/2004 | Miller et al. |
| 2004/0035420 | A1 | 2/2004 | Davies et al. |
| 2004/0151059 | A1 | 8/2004 | Roberts, II et al. |
| 2004/0182387 | A1 | 9/2004 | Steiner et al. |
| 2004/0187868 | A1 | 9/2004 | Hochrainer et al. |
| 2004/0206773 | A1 | 10/2004 | Ede et al. |
| 2004/0211419 | A1 | 10/2004 | Eason et al. |
| 2004/0251318 | A1 | 12/2004 | Braithwaite |
| 2004/0255940 | A1 | 12/2004 | Pera |
| 2005/0039743 | A1 | 2/2005 | Taylor |
| 2005/0056276 | A1 | 3/2005 | Schuler et al. |
| 2005/0066961 | A1 | 3/2005 | Rand |
| 2005/0081851 | A1 | 4/2005 | Young et al. |
| 2005/0081853 | A1 | 4/2005 | Young et al. |
| 2005/0087188 | A1 | 4/2005 | Young et al. |
| 2005/0121032 | A1 | 6/2005 | Nilsson et al. |

FOREIGN PATENT DOCUMENTS

| | | | |
|---|---|---|---|
| GB | 2242134 | A | 9/1991 |
| GB | 2264237 | A | 8/1993 |
| GB | 2 426 202 | A | 11/2006 |
| WO | WO92/05823 | A1 | 4/1992 |
| WO | WO9324166 | A2 | 12/1993 |
| WO | WO 97/40876 | A2 | 11/1997 |
| WO | WO 97/40876 | A3 | 11/1997 |
| WO | WO0043059 | A1 | 7/2000 |
| WO | WO03015857 | A1 | 2/2003 |
| WO | WO 03061744 | A1 * | 7/2003 |
| WO | WO2004045688 | A1 | 6/2004 |
| WO | WO2005049121 | A1 | 6/2005 |
| WO | WO2005123002 | | 12/2005 |
| WO | WO2006031775 | A2 | 3/2006 |
| WO | WO2006031775 | A3 | 3/2006 |

OTHER PUBLICATIONS

Hickey et al. "A New Millennium for Inhaler Technology" *Pharmaceutical Technology* 21(6):7 pages (1997).

Hovione "FlowCaps® Introduction" 1 pages (2005) <http://www.flowcaps.com/inf_pack.htm>.

Hovione FlowCaps® "Patents and Trademarks" 1 page (2005) http://www.flovvcaps.corn/patents,htm.

Invitation to Pay Additional Fees for PCT/US2007/001762; Aug. 1, 2007.

Peart et al. "New Developments in Dry Powder Inhaler Technology" *American Pharmaceutical Review* 4(3):37-45 (2001).

Prime et al. "Review of dry powder inhalers" *Advanced Drug Delivery Reviews* 26:51-58 (1997).

Wolff et al. "Generation of Aerosolized Drugs" *Journal of Aerosol Medicine* 7(1):89-106 (1994).

International Search Report and Written Opinion for PCT/US2007/001762; Nov. 9, 2007.

* cited by examiner

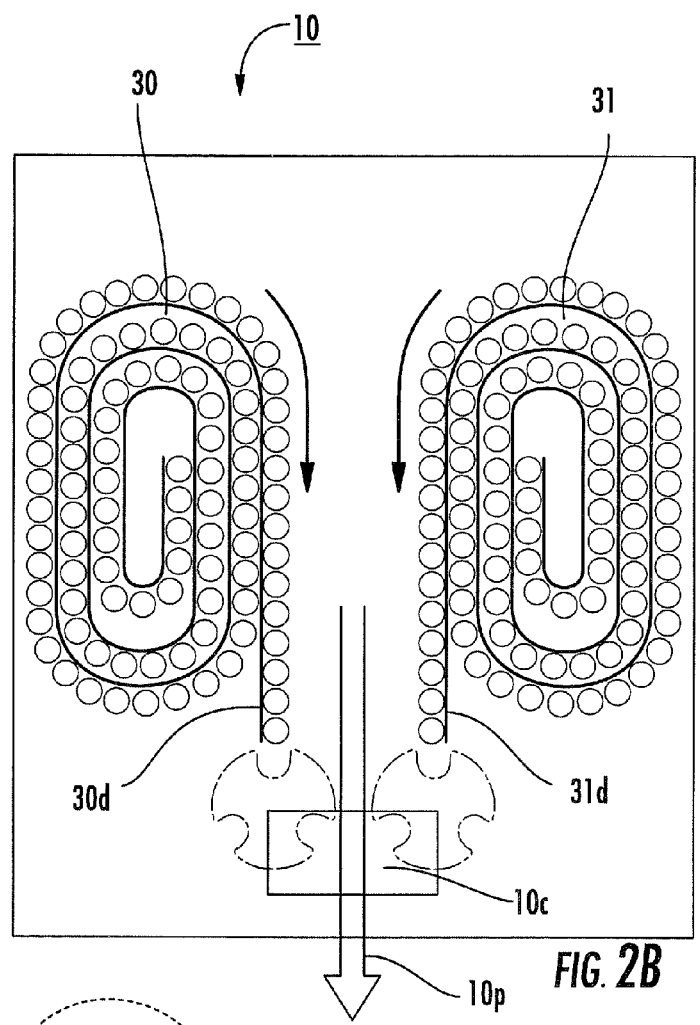
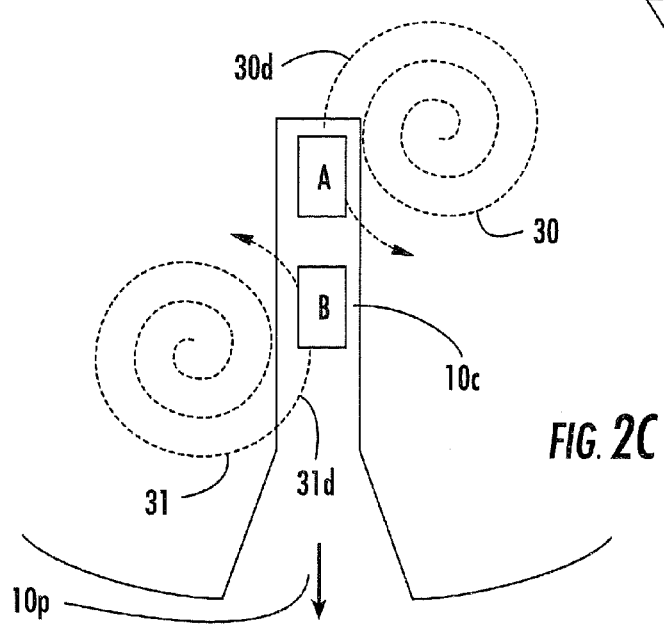

DRY POWDER INHALERS HAVING SPIRAL TRAVEL PATHS, UNIT DOSE MICROCARTRIDGES WITH DRY POWDER, RELATED DEVICES AND METHODS

RELATED APPLICATIONS

This application claims the benefit of priority to U.S. Provisional Application Ser. No. 60/763,717, filed Jan. 31, 2006, the contents of which are hereby incorporated by reference as if recited in full herein.

FIELD OF THE INVENTION

The present invention relates to drug containment and/or dispensing systems suitable for dry powders formulated for delivery as inhalant aerosols.

BACKGROUND OF THE INVENTION

Dry powder inhalers (DPIs) represent a promising alternative to pressurized pMDI (pressurized metered dose inhaler) devices for delivering drug aerosols without using CFC propellants. See generally, Crowder et al., 2001: *an Odyssey in Inhaler Formulation and Design*, Pharmaceutical Technology, pp. 99-113, July 2001; and Peart et al., *New Developments in Dry Powder Inhaler Technology*, American Pharmaceutical Review, Vol. 4, n. 3, pp. 37-45 (2001). Typically, the DPIs are configured to deliver a powdered drug or drug mixture that includes an excipient and/or other ingredients.

Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers,* 26 Adv. Drug Delivery Rev., pp. 51-58 (1997); and Hickey et al., *A new millennium for inhaler technology,* 21 Pharm. Tech., n. 6, pp. 116-125 (1997).

In operation, DPI devices strive to administer a uniform aerosol dispersion amount in a desired physical form of the dry powder (such as a particulate size) into a patient's airway and direct it to a desired deposit site(s).

A number of obstacles can undesirably impact the performance of the DPI. For example, the small size of the inhalable particles in the dry powder drug mixture can subject them to forces of agglomeration and/or cohesion (certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, some dry powder inhalers can retain a significant amount of the drug within the device, which can be especially problematic over time.

Some inhalation devices have attempted to resolve problems attendant with conventional passive inhalers. For example, U.S. Pat. No. 5,655,523 proposes a dry powder inhalation device which has a deagglomeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. U.S. Pat. No. 5,533,502 to Piper proposes a powder inhaler using patient inspiratory efforts for generating a respirable aerosol and also includes a rotatable cartridge holding the depressed wells or blisters defining the medicament-holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. U.S. Pat. No. 6,971,383 to Hickey et al. and U.S. Pat. No. 6,889,690 to Crowder et al. describe using custom signals matched to a particular dry powder to facilitate fluidic delivery. The contents of all of these patents are hereby incorporated by reference as if stated in full herein.

Notwithstanding the above, there remains a need for alternative inhalers and/or drug containment devices that can be used to deliver dry powder medicaments.

SUMMARY OF EMBODIMENTS OF THE INVENTION

Dry powder inhalers include: (a) a first generally planar spiral travel path in an inhaler body, wherein the first spiral travel path has a plurality of adjacent curvilinear channels forming lanes with upstanding sidewalls, including an inner lane and an outer lane; and (b) a plurality of discrete sealed microcartridges with substantially rigid bodies disposed in the first travel path, each comprising a pre-metered dose of dry powder, the microcartridges being configured to slidably advance along the first travel path toward an inhalation chamber that merges into an inhalation output port, wherein, in operation, at least one microcartridge is held in the inhalation chamber to release the dry powder therein during inhalation.

Other embodiments are directed to dry powder inhalers that include: (a) first and second curvilinear travel paths in an inhaler body, at least a major portion of one residing above the other, each curvilinear travel path comprising a plurality of curvilinear side-by-side lanes on a common plane, the curvilinear travel paths comprising a respective dispensing lane that leads to an inhalation delivery chamber in fluid communication with an inhalation port; and (b) a plurality of discrete microcartridges, each comprising a meted amount of dry powder, wherein microcartridges disposed in each of the first and second travel path snugly about neighboring microcartridges and slidably advance along the respective travel paths to the respective dispensing lane.

Still other embodiments are directed to methods of operating an inhaler to expel inhalable medicaments. The methods include: slidably advancing a plurality of snugly abutting sealed microcartridges loaded with a meted amount of a first dry powder along a first curvilinear channel associated with a first travel path so that at least some of the respective loaded microcartridges travel greater than one revolution in a first level.

In particular embodiments, the method may optionally include directing the loaded microcartridges to travel to a lower level for dispensing in an inhalation chamber after traveling greater than one revolution in the first level.

In some embodiments, the first travel path channel defines closely spaced serially traveled spiraling travel lanes, wherein at least some of the microcartridges travel greater than 2 revolutions in a first level in the spiraling lanes before moving to a second level for dispensing.

Additional embodiments are directed to methods of forming unit dose microcartridges for use in dry powder inhalers. The methods include: (a) providing a substantially rigid elastomeric microcartridge body; (b) inserting a meted amount of dry powder suitable for inhalation delivery; and (c) attaching a substantially rigid top to the body to seal the dry powder therein.

The methods may optionally include providing externally visible indicia of dry powder type and/or dose amount on the body.

It is noted that aspects of the invention may be embodied as hardware, software or combinations of same, i.e., devices, methods and/or computer program products. These and other objects and/or aspects of the present invention are explained in detail in the specification set forth below.

BRIEF DESCRIPTION OF THE FIGURES

FIG. 2B is a schematic illustration of side-by-side spiral travel paths according to other embodiments of the present invention.

FIG. 2C is a schematic illustration of an alternate spiral travel path configuration according to other embodiments of the present invention.

DESCRIPTION OF EMBODIMENTS OF THE INVENTION

Figure 1:
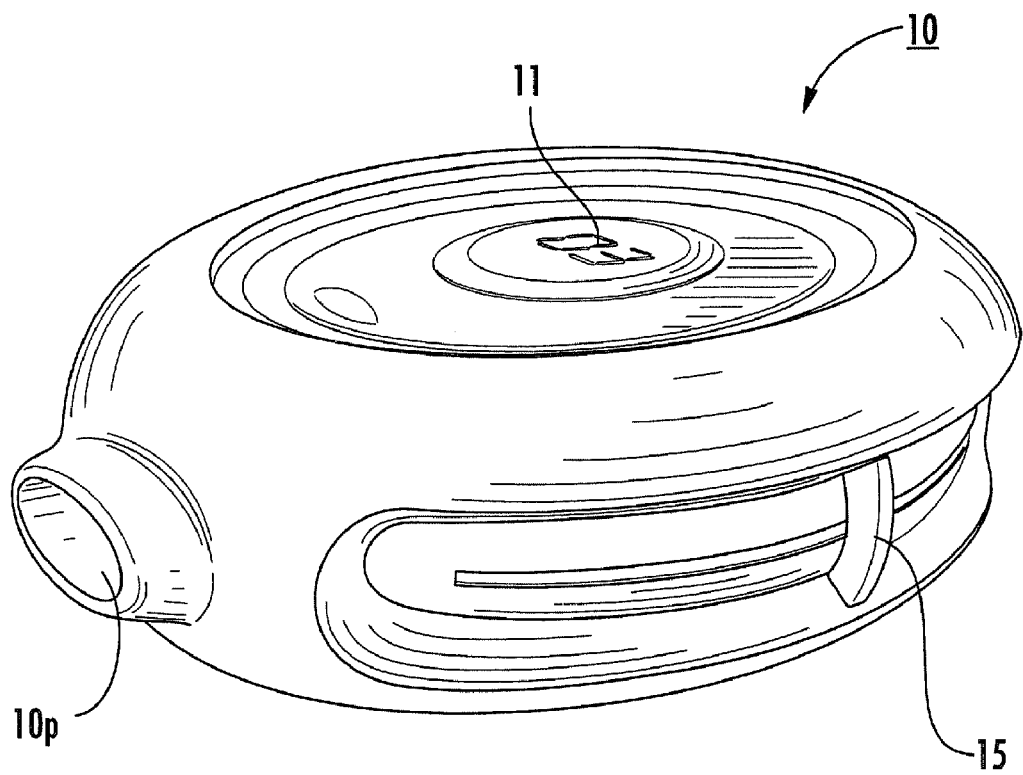
FIG. 1 is a side perspective view of an exemplary inhaler according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this application and should not be interpreted in an idealized or overly formal sense unless expressly so defined herein.

In the description of the present invention that follows, certain terms are employed to refer to the positional relationship of certain structures relative to other structures. As used herein, the term "front" or "forward" and derivatives thereof refer to the general or primary direction that the dry powder travels to be dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "sealant layer" and/or "sealant material" includes configurations that have at least one layer or one material; thus, such a phrase also includes multi-layer or multi-material sealant configurations. The term "unitized" means a specified quantity of a pharmaceutical drug and/or medicament in terms of which the magnitudes of other quantities of the same or different drug and/or medicament can be stated.

The term "deagglomeration" and its derivatives refer to processing dry powder in the inhaler airflow path to inhibit the dry powder from remaining or becoming agglomerated or cohesive during inspiration.

The term "microcartridge" and derivatives thereof refer to a disposable drug container device that holds at least one unitized, meted and/or bolus amount of a target drug or medicament and may be also known as a drug containment system ("DCS"). The microcartridges can be configured as relatively compact, generally tubular and/or cup-like containers with a cavity that is sized and configured to hold about 100 mg or less of dry powder for inhalation delivery, typically less than 50 mg, and more typically between about 0.1 mg to about 10 mg. In some embodiments, such as for pulmonary conditions (i.e., asthma), the dry powder can be provided as about 5 mg total weight (the dose amount may be blended to provide this weight). The microcartridges can have sidewalls with sufficient rigidity to resist flexure and allow a ceiling to be sealably attached thereto after filling. The microcartridges are configured to inhibit oxygen and moisture penetration. In particular embodiments, the microcartridges can be configured to have a miniaturized "puck" shape, such that they may be wider than they are tall with a hollow interior or holding cavity. In other embodiments, the microcartridges may have a similar height and width or may be taller than they are wide.

The term "free floating" refers to embodiments where the microcartridges are detached (not connected) from each other.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents or ingredients with one or a plurality of (average) particulate size ranges. The term "low-density" dry powder means dry powders having a density of about 0.8 g/cm$^3$ or less. In particular embodiments, the low-density powder may have a density of about 0.5 g/cm$^3$ or less. The dry powder may be a dry powder with cohesive or agglomeration tendencies.

In any event, individual dispensable quantities of dry powder formulations can be a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50 μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroid, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhalers may vary depending on the patient size, the systemic target, and the particular drug(s). A conventional exemplary dry powder dose amount for an average adult is less than about 50 mg, typically between about 10-30 mg and for an average adolescent pediatric subject is typically from about 5-10 mg. A typical dose concentration may be between about 1-2%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 µg-10 mg, and more typically between about 50 µg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 µg.

In certain particular embodiments, during dose dispensing, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the unit dose amount of dry powder held in a respective microcartridge is less than about 10 mg, typically about 5 mg of blended drug and lactose or other additive (e.g., 5 mg LAC), for treating pulmonary conditions such as asthma. Insulin may be provided in quantities of about 4 mg or less, typically about 3.6 mg of pure insulin. The dry powder may be inserted into a microcartridge (or capsule or other suitable container) in a "compressed" or partially compressed manner or may be provided as free flowing particulates.

Some embodiments of the invention are directed to inhalers that can deliver multiple different drugs for combination delivery. For example, the inhalers can be configured to provide 60 doses of two different drugs (in the same or different unit amounts) for a total of 120 individual unit doses. This typically equates to a 30-day or 60-day supply. In other embodiments, the inhalers can be configured to hold 120 doses of the same drug, in the same or different unit amounts, which can be a 120-day supply (for single daily treatments).

Turning now to the figures, FIG. 1 illustrates an example of a multi-dose inhaler 10. The inhaler 10 is typically disposable after its pre-loaded medicines are dispensed. However, in certain embodiments, the inhaler can be reloaded by a manufacturer, pharmacist or by the use. The inhaler 10 includes an inhalation port 10*p*. The inhaler 10 can include an actuator (shown as an externally accessible lever) 15 that can be used to activate the device. The actuator 15 can comprise a knob, switch, slider, crank or other mechanical or electromechanical device. As will be discussed below, in some embodiments, the actuator 15 can be used to advance a microcartridge 25 (FIG. 2A) into position in an inhalation chamber 10*c* (FIGS. 6A and 7) in fluid communication with the inhalation port 10*p*. In other embodiments, the actuator 15 may reside internal to the device and an electronic switch (i.e., on/off switch) can be used to activate the device and/or actuator 15. However, as noted above, in other embodiments, other mechanisms that do not require levers or that employ alternate configurations of levers may be used to activate and/or deploy a microcartridge 25 (FIG. 2A) into position in the inhalation chamber 10*c*.

In some embodiments, the mouthpiece port 10*p* and an air inlet port (not shown) may be spaced apart about a distance of between about 12-127 mm (about 0.5-5 inches). The inhaler 10 may have a relatively short air intake airpath (measured from where an air intake is disposed to the inhalation port 10*p*), such as between about 12-25.4 mm, or a longer airpath, and typically between about 50-127 mm (about 2-5 inches). The shorter airpath can be defined to include a short tubular airpath extending between the dry powder release location and the inhalation mouthpiece with a turbulence promoter segment that inhibits agglomeration that merges into the inhaler mouthpiece (not shown). The longer airpath may extend across a major portion or substantially all of a width or length of the inhaler body. For a more detailed discussion of suitable turbulence promoter configurations, see PCT/US2005/032492, entitled, Dry Powder Inhalers That Inhibit Agglomeration, Related Devices and Methods, the contents of which are hereby incorporated by reference as if recited in full herein.

The inhaler 10 can have a body that is a portable, relatively compact "pocket-sized" configuration. In some embodiments, the inhaler body can have a width/length that is less than about 115 mm (about 4.5 inches), typically less than about 89 mm (about 3.5 inches), and a thickness/depth of less than about 51 mm (about 2 inches), typically less than about 38 mm (about 1.5 inches). The inhaler body can also be configured to be generally planar on opposing primary surfaces to facilitate pocket storage.

The inhaler 10 can also include a display 11 and, optionally, a user input. The display 11 can indicate the number of doses remaining or the number of doses used. The user input may include a "+" and a "−" input key (not shown). The user input can comprise contact pads, a touch screen or other input means, including a numeric entry device which can be used to track the amount of unitized bolus amounts of a target bolus amount of a drug needed by a user.

Figure 2A:
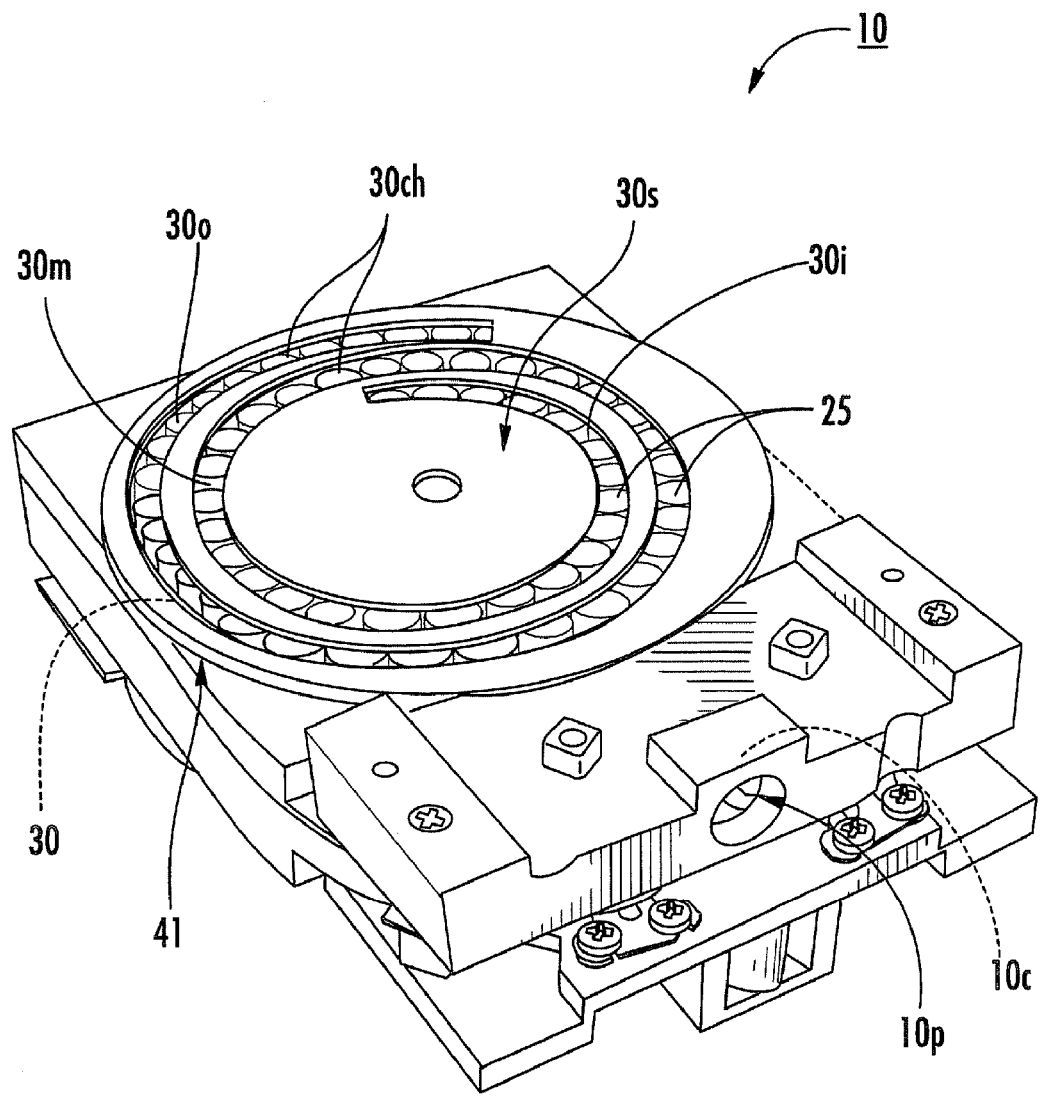
FIG. 2A is a side perspective view of an internal portion of a multi-level inhaler with dual spiral travel paths according to embodiments of the present invention.
Figure 3A:
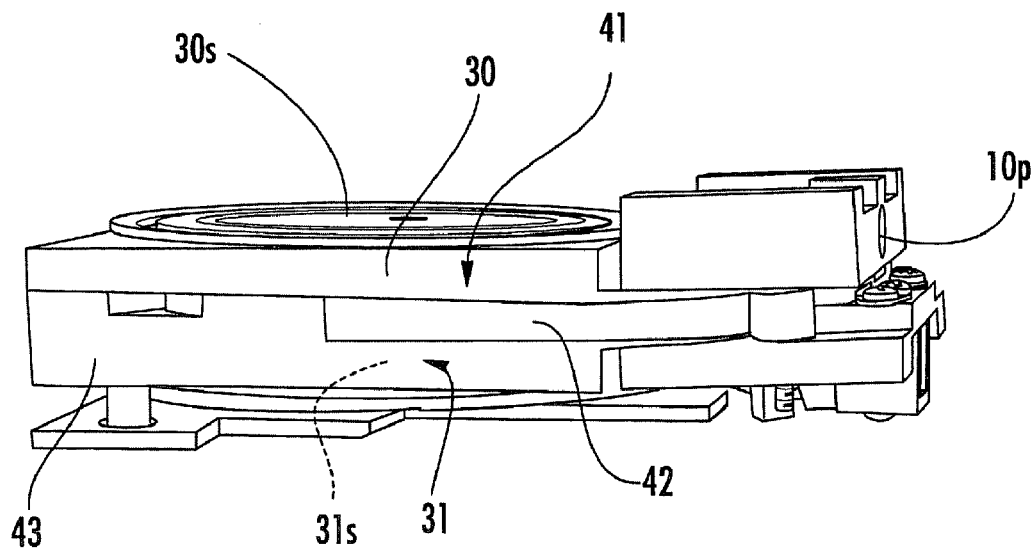
FIG. 3A is a side view of an internal portion of a multi-level inhaler according to embodiments of the present invention.
Figure 3B:
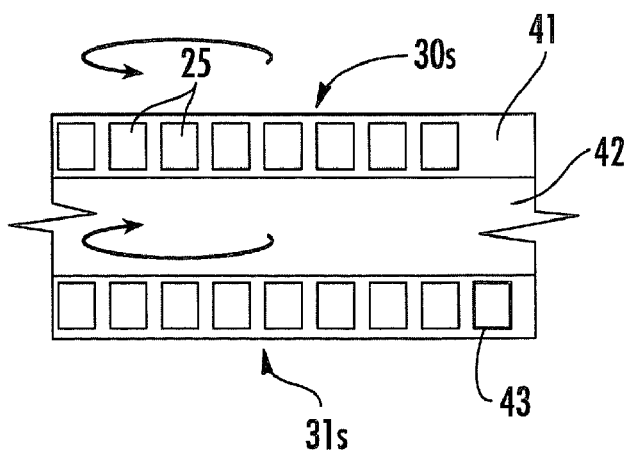
FIG. 3B is a schematic side view of a portion of an inhaler with multi-level queues of discrete drug containers according to embodiments of the present invention.
Figure 4A:
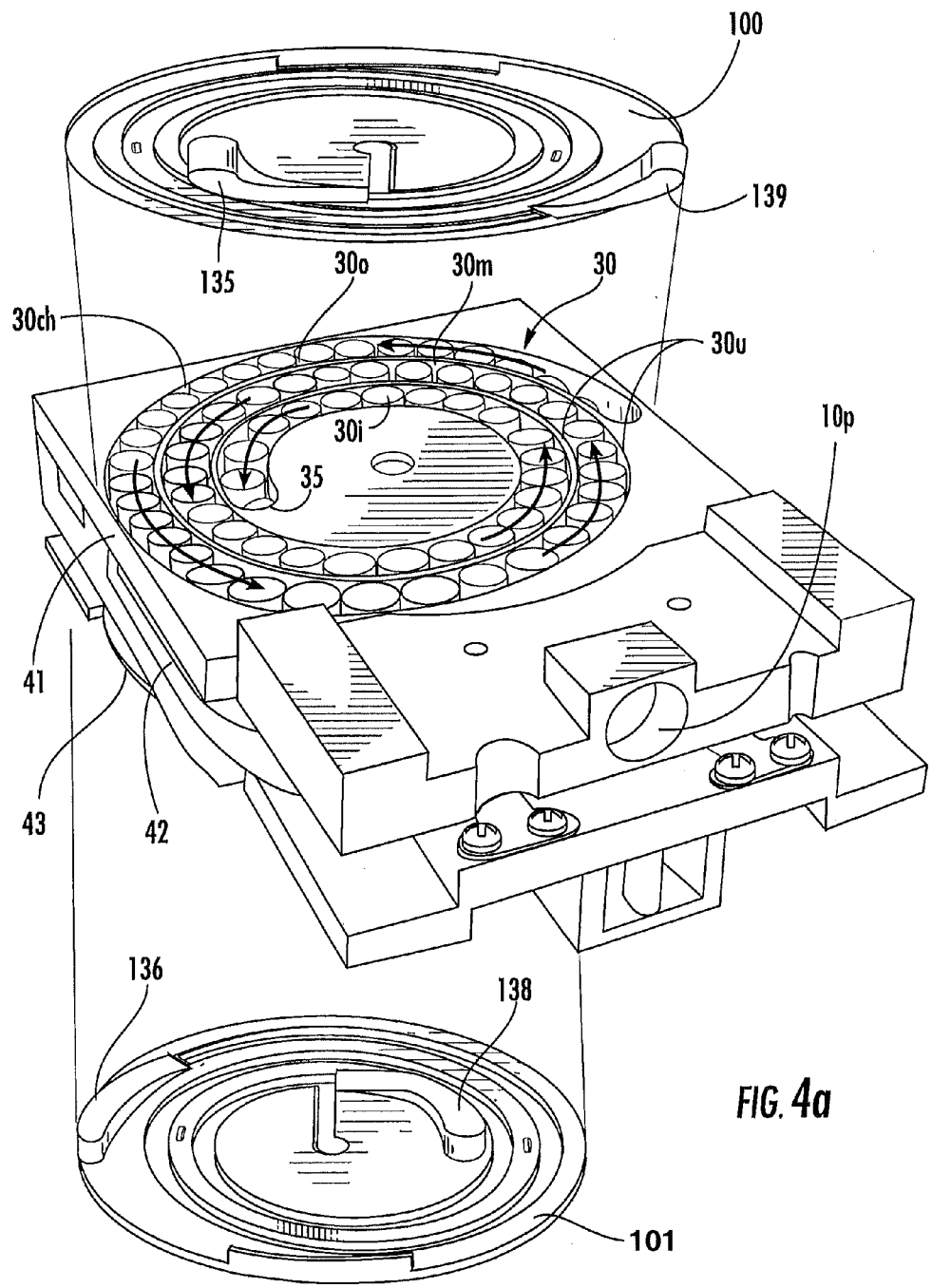
FIG. 4A is an exploded top perspective view of an inhaler with a curvilinear drug travel path according to embodiments of the present invention.
Figure 5:
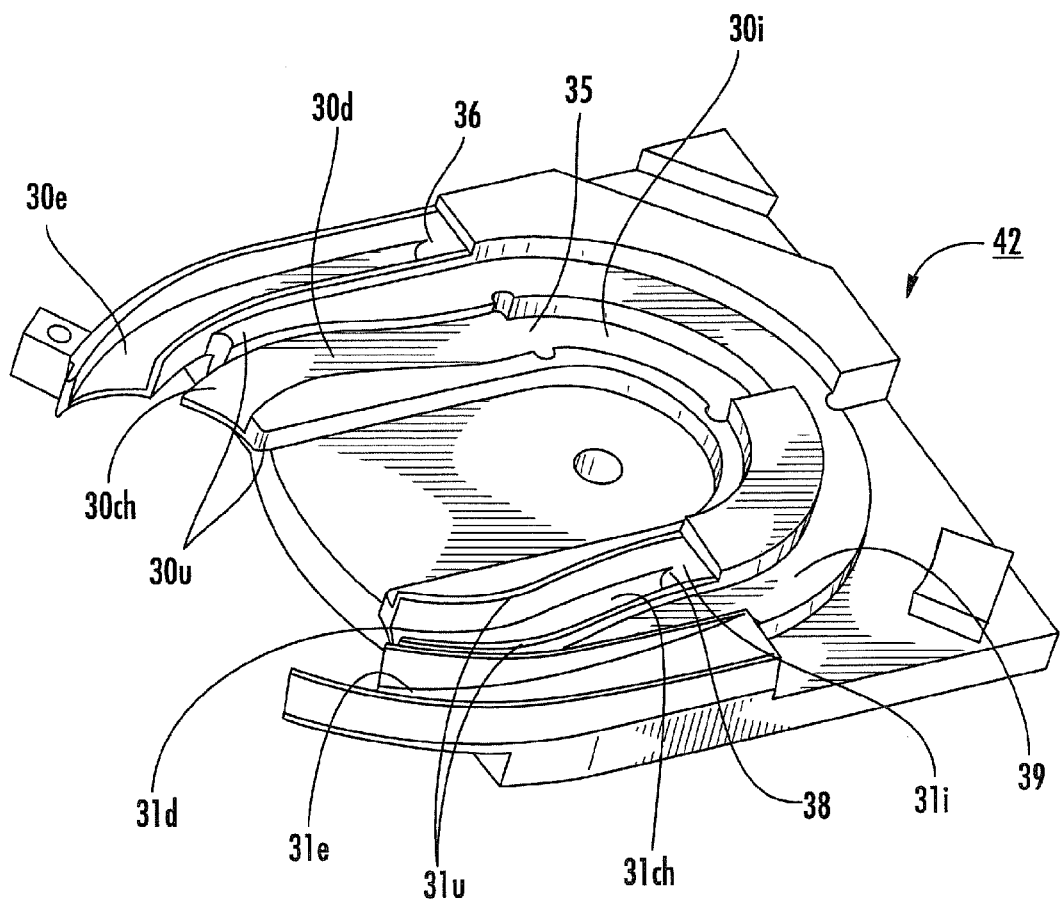
FIG. 5 is a side perspective view of a portion of a dispensing floor of a multi-level inhaler according to embodiments of the present invention.
Figure 6A:
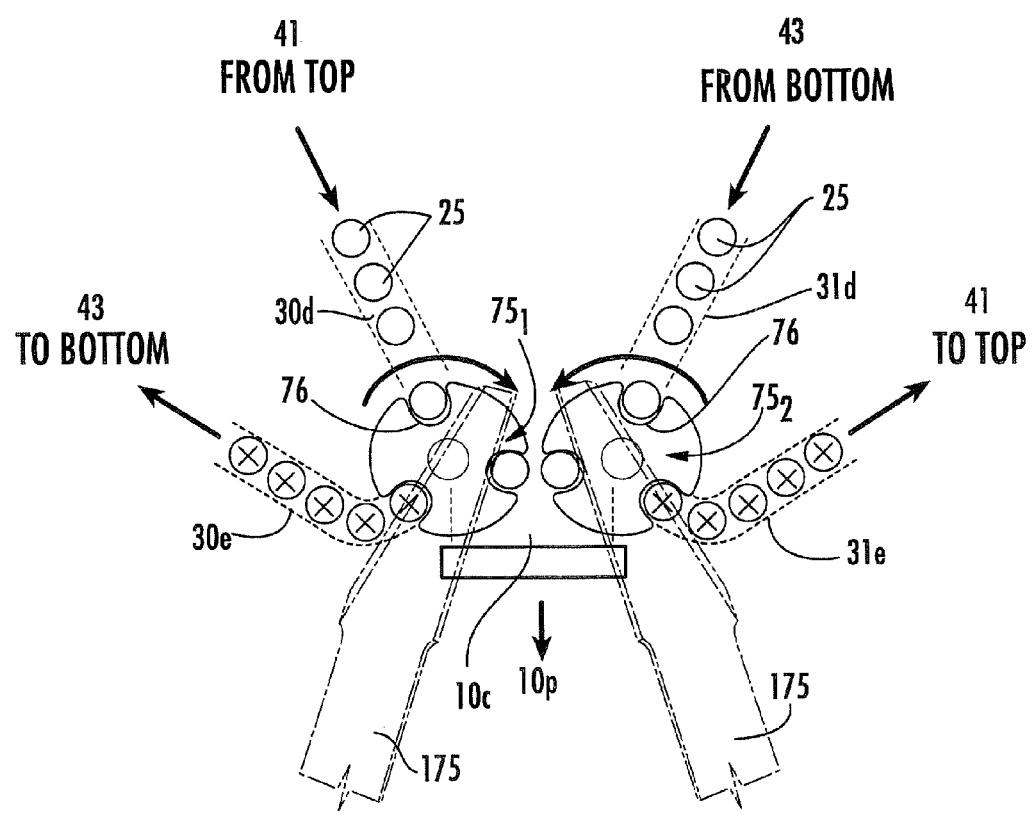
FIG. 6A is a schematic illustration of an intake and release path for dispensing combination delivery inhalation medicaments in an inhaler according to embodiments of the present invention.

FIG. 2A illustrates that the inhaler 10 can include a first primary travel path 30 having a curvilinear segment 30*s* (typically a spiraling segment) with an inner lane 30*i* and outer lane 30*o*, and as shown, a medial lane 30*m*. Additional or lesser numbers of lanes may be used. Each lane is defined by a channel 30*ch* that is sized and configured to hold the microcartridges 25 in single-file formation. The channel 30*ch* typically includes upstanding sidewalls 30*u* (FIG. 4A) and a floor and the microcartridges 25 can slide along the channel 30*ch*, traveling counterclockwise from the outer lane to the inner lane to a dispensing position in the inhalation chamber 10*c*. Alternatively, the microcartridges 25 can be configured to travel clockwise with the dispensing path adjusted accordingly. The curvilinear segment 30*s* may include a substantially horizontal orientation as shown.

The microcartridges 25 can be captured in the channel 30*ch* and configured to slidably advance therein. The microcartridges 25 may be configured to reside above the floor or may slidably travel over the floor. As shown, at least a majority of the microcartridges 25 snugly abut neighboring microcartridges 25. "Dummy" (empty microcartridges or "blank" members) can be used in certain locations of the travel path (such as after the last "full" microcartridge). As will be discussed further below, one or more compression springs 125 (FIG. 12) can be placed in the channel 30*ch* and move with the proximately positioned members along the travel path 30. The compression spring 125 can provide kinetic energy that can help push the forward cartridges along.

In operation, the inhaler 10 is loaded with "full" microcartridges 25. It is noted that the term "full" refers to the container having a desired amount, which may not completely fill the internal sealed volume of the container 25. The microcartridges 25 are configured to slidably advance in the first travel path channel 30*ch* with the outer lane 30*o* merging into the medial lane 30*m*, which merges to the inner lane 30*i*.

Thus, the first primary travel path 30 can hold a queue of loaded microcartridges 25 on a first level 41 (such as an upper level) of an inhaler 10. At least some of the loaded or full microcartridges 25, including those in the medial and outer lanes, 30*m*, 30*o*, can serially travel greater than one revolution in a first tier or level of the inhaler 10 before advancing to the dispensing lane and into the inhalation chamber 10*c*. The tier or level can be substantially planar or may be non-planar. Those microcartridges 25 pre-loaded in the inner lane 30*i* can travel a lesser distance than those upstream thereof, such as about one or less than one revolution before traveling into the dispensing channel (30*d*, FIGS. 5, 6). The full microcartridges 25 pre-loaded in the outer lane 30*o* will travel further than the full microcartridges 25 pre-loaded on the medial or inner lanes 30*m*, 30*i*, respectively.

FIG. 2B illustrates that the inhaler 10 can include side-by-side travel paths 30, 31 (rather than and/or in a addition to the multi-level paths shown in FIG. 2A). As shown, at least a major portion of the two paths 30, 31 can be substantially coplanar. The spirals 30*s*, 31*s*, may be elongated relative to that shown in FIG. 2A and the direction of travel may be from inner to outer lane rather than from outer to inner lane as discussed herein with respect to the embodiment shown in FIG. 2A. The empty microcartridges 25 as well as cut remnants may be redirected to the back of a queue or to a trash bin (internal or externally accessible) or may be expelled from the inhaler not shown).

FIG. 2C illustrates a top schematic view of another exemplary travel path configuration. As shown, at least a portion of one travel path 30 is behind the other 31, with the dispensing lanes 31*d*, 30*d* meeting in the inhalation chamber 10*c*. Again, at least a major potion of the travel paths 30, 31 may reside on a common plane.

FIG. 3A illustrates that the inhaler 10 can include three levels, 41, 42, and 43. An exemplary upper level 41 has been described above. The lower level 43 can include a second primary travel path 31 with a curvilinear channel 31*ch* with sidewalls 31*u* (FIG. 5), configured substantially the same as that of the first primary travel path 30. In operation, loaded or full microcartridges 25 are pre-loaded in each path 30, 31 and full microcartridges 25 travel in one of the channels 30*ch*, 31*ch* along at least a portion of the respective curvilinear lanes 31*s*, 30*s*. In some embodiments, as shown in FIG. 3B, microcartridges 25 traveling the first level 41 can travel counterclockwise while those traveling the second level 42 can travel clockwise. The travel can be reversed for the curvilinear portion of each path 30, 31 (not shown). In other embodiments, the travel in each curvilinear portion of the paths can be the same direction (also not shown).

Microcartridges 25 from each respective path 30, 31 can travel substantially in concert to be delivered concurrently or serially to a respective dispensing lane 30*d*, 31*d* (FIGS. 5 and 6A), opened, then moved in concert or serially into the inhalation chamber 10*c* for inhalation delivery. The use of dual primary paths 30, 31 can allow for increased density loading of microcartridges 25, and/or combination drug delivery. It is also noted that, although shown as a three-tier or three-level inhaler 10, a single or dual level configuration, additional levels (i.e., 4 or more), and/or a single travel path (with increased or the same number of microcartridges) rather than dual paths may be used.

Referring to FIG. 4A, in some embodiments, the first path inner lane 30*i* includes a downwardly oriented ramp 35 that travels down to merge into the dispensing lane 30*d* (FIGS. 5 and 6A) located at a level 42, which may be under the upper level 41 of the inhaler 10. Similarly, the second path inner lane 31*i* can include a ramp 39 that travels up to merge into the dispensing lane 31*d* located at level 42. As shown in FIG. 5, the dispensing lanes 30*d*, 31*d* travel side by side and travel toward each in the direction of the holders 75 (FIG. 6A).

As also shown, the inhaler 10 can include a lid 100 that overlies the channel 30*ch* and attaches to the first path 30 to define a ceiling over the channel 30*ch*. The lid 100 can include a ramp segment 135 with increasing depth in the travel direction that overlies the ramp 35. The inhaler 10 can also include a floor 101 that underlies the channel 31*ch* and attaches to the second path 31. The floor 101 can include a ramp segment 138 with increasing height in the direction of travel that underlies the ramp 39. The ramp segment 138 extends up into the inner lane 31*i* to hold the microcartridges 25 in the channel 31*ch* and direct the microcartridges 25 to travel up the ramp 38. As shown in FIGS. 4A and 5, the inhaler 10 also includes a corresponding ramp segment 136 and ramp 36, the ramp 36 associated with return lane 30*e*.

Figure 4B:
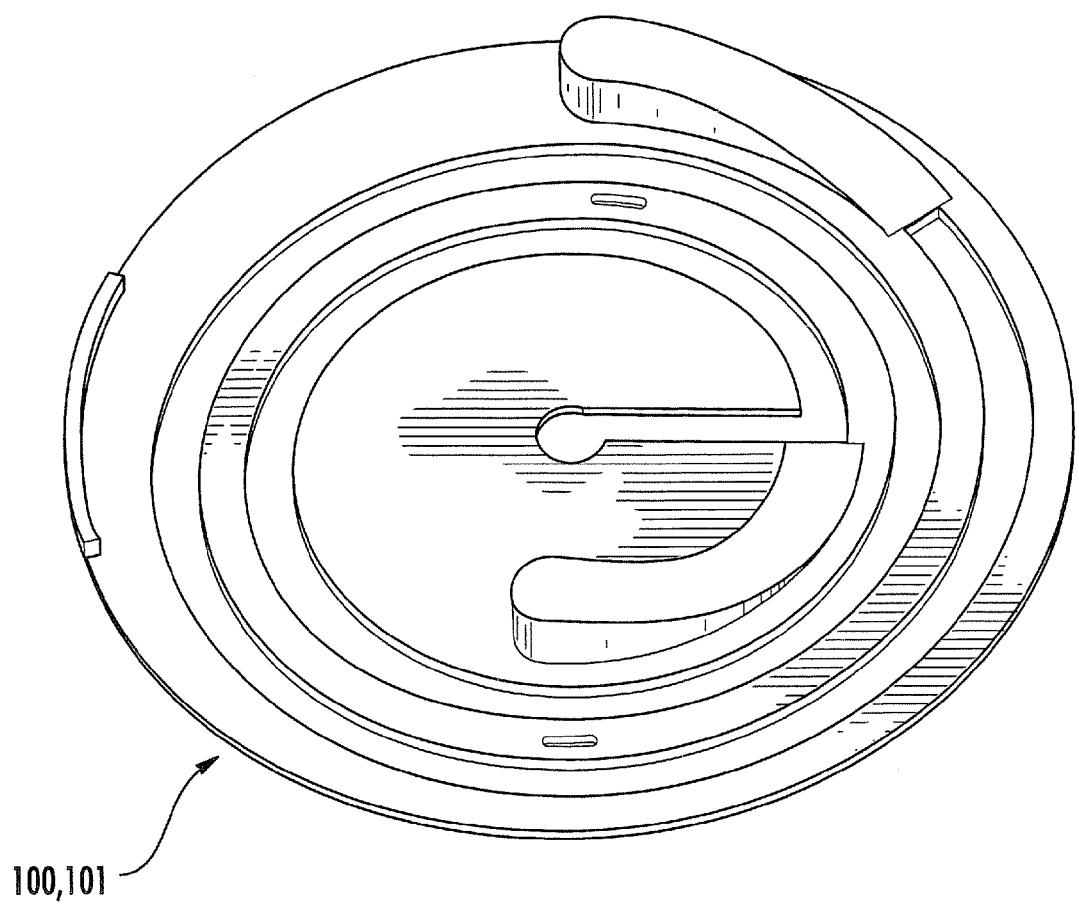
FIG. 4B is an enlarged side perspective view of a portion of an inhaler according to embodiments of the present invention.
Figure 4C:
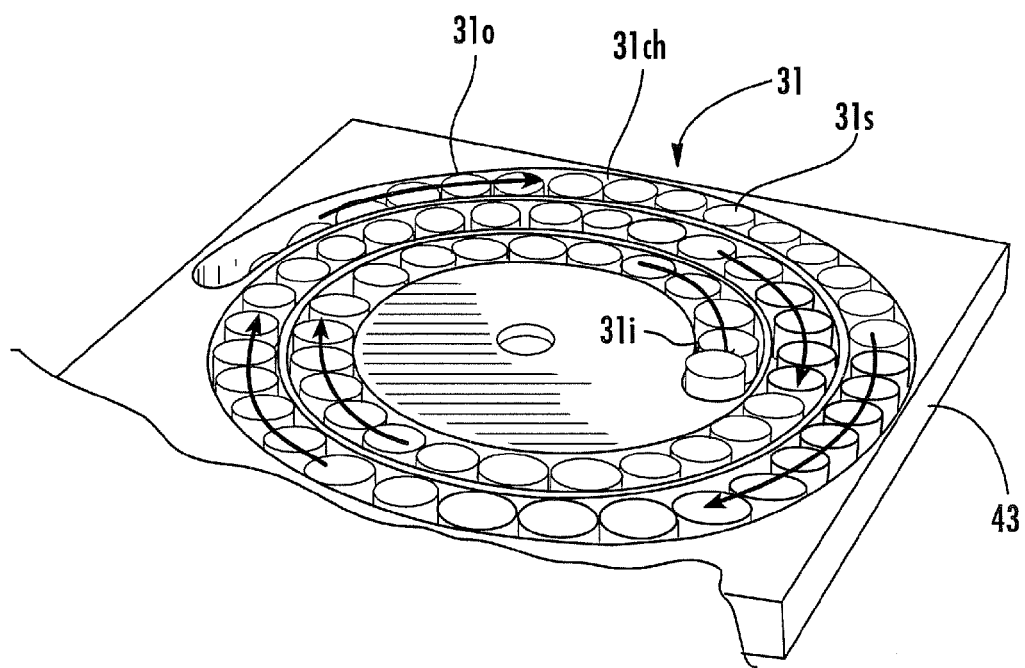
FIG. 4C is a cutaway view of a lower level of a multi-level inhaler according to some embodiments of the present invention.

In some embodiments, as shown in FIG. 4B, the levels 41 and 43 can be symmetrically configured so that the lid and floor 100, 101, respectively can have substantially the same configuration. To use as the lid 100, the member is turned so that the ramps are oriented downward and aligned with and secured to channel 30*ch*; to use as the floor 101, the member is turned so that the ramps are oriented upward and aligned with and secured to the adjacent channel 31*ch*. Similarly, in some embodiments, the layers 41 and 42 and associated curvilinear segments 30*s*, 31*s* are symmetrical. In contrast to level 41, the inner lane 31*i* travels up to the level 42 and the return lane from level 42 travels down to outer lane 31*o* at level 43. The inner lanes of each layer 41, 42 merge into the respective dispensing lanes 30*d*, 31*d* at level 42. FIG. 4C illustrates the configuration of layer 43, with the microcartridges traveling clockwise under the layer 41.

Figure 7:
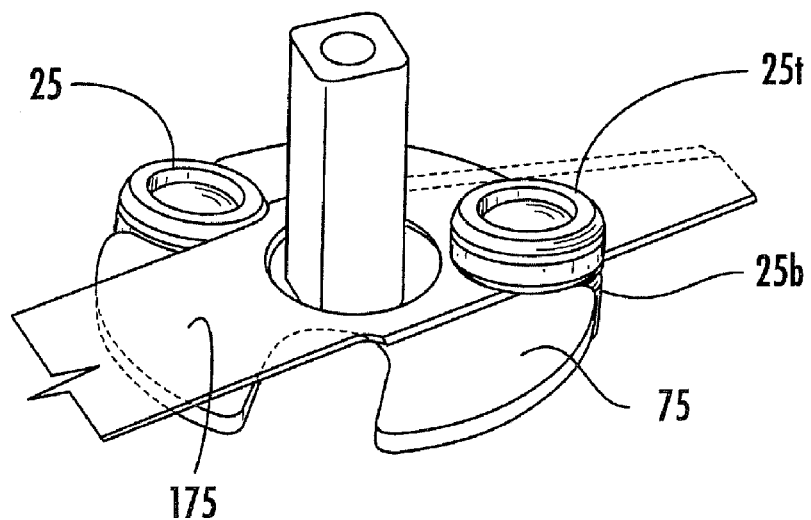
FIGS. 7 and 8 are schematic illustrations of a cutting operation according to embodiments of the present invention.
Figure 8:
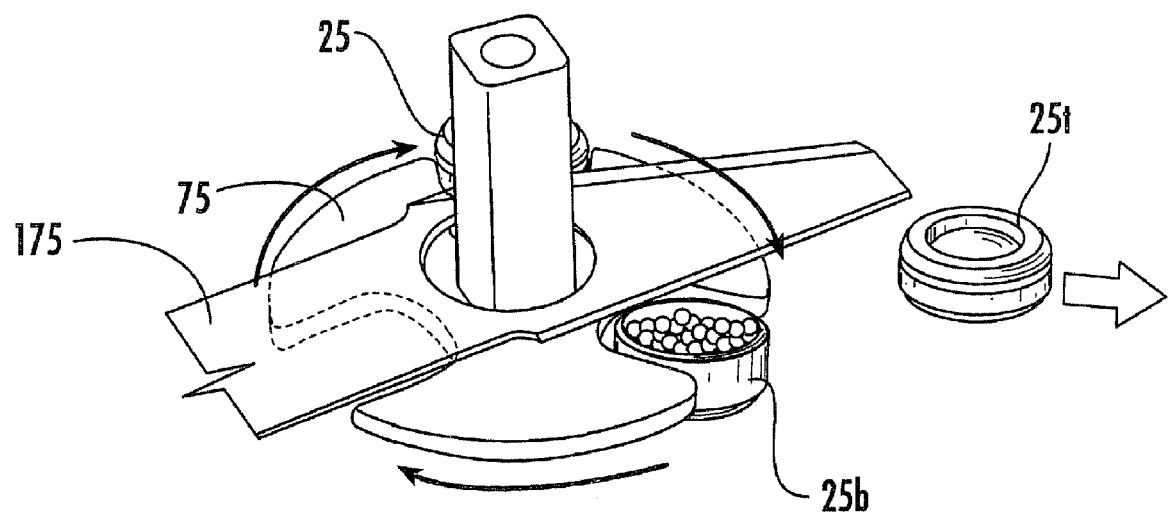

In some particular embodiments, the inhaler 10 can be configured to concurrently dispense combinations of drugs, one from a respective microcartridge 25 from each path 30, 31. As shown in FIG. 6A, microcartridges 25 travel along one of the dispensing lanes 30*d*, 31*d* to a respective rotating holder 75. The holder 75 includes at least one receiver 76 that releasably receives a microcartridge 25. As shown, each holder 75 has three equally spaced (120 degrees from center to center) receivers 76, but lesser or greater numbers may be used. The holder 75 rotates to advance the microcartridge 25 held in a respective receiver 76 against a blade 175 to cut open the microcartridge 25. Typically, the blade 175 cuts an entire top portion off the microcartridge 25. FIGS. 7 and 8 illustrate the top portion of the microcartridge 25*t* being cut off the body 25*b* according to some embodiments of the invention. In other embodiments, the top portion 25*t* may be otherwise opened or removed, and may include other openable configurations, such as a peelable sealant layer, a piercing or puncturing layer or a removable sealant (not shown). Of course, the microcartridge 25 may also be cut at different locations than shown. For example, the blade can cut off a lower portion of the body. Alternatively, instead of having the cutting blade 175 above or below the holder 75, the holder 75 may enclose or hold a greater portion of the microcartridge body therein. As such, the holder 75 may include a slot that allows the blade 175 to cut across the microcartridge 25 through the holder (not shown).

Figure 10:
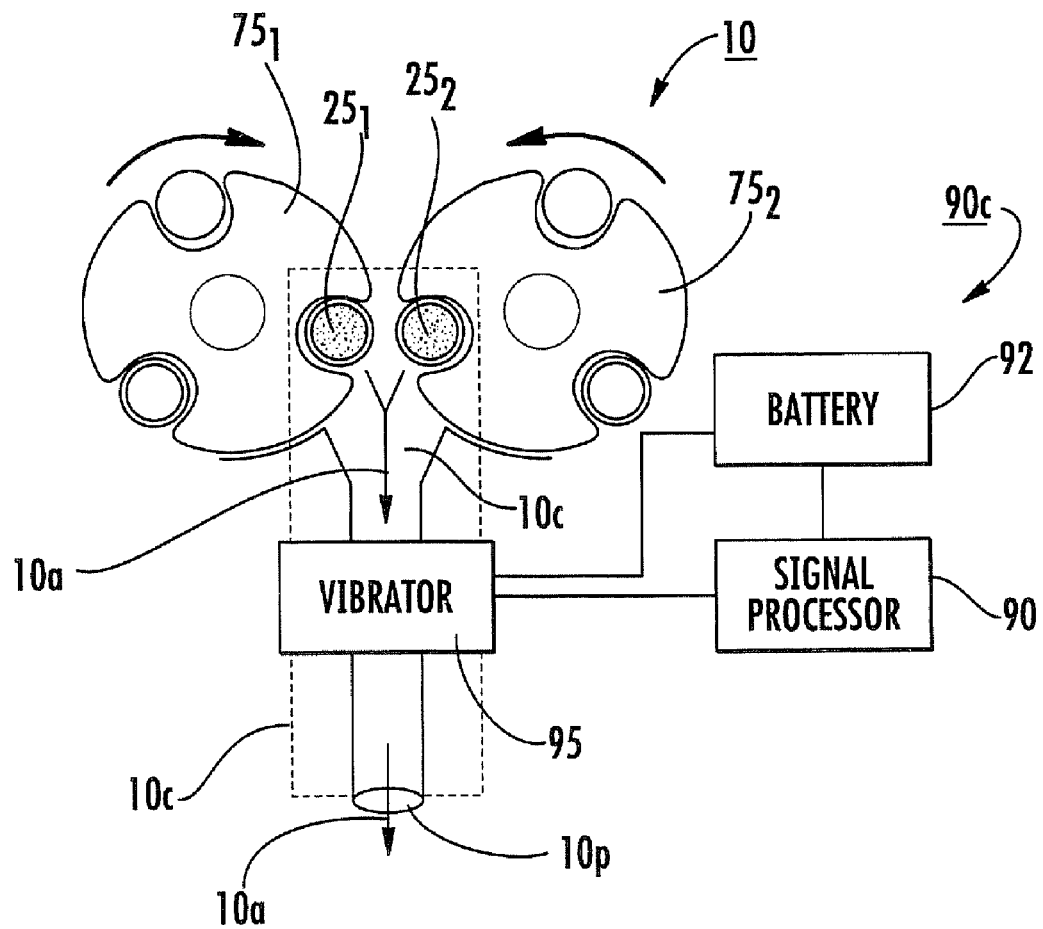
FIG. 10 is a schematic illustration of a circuit for an inhaler usable for a combination delivery system according to embodiments of the present invention.

Referring again to FIG. 6A, after opening, the rotating holder 75 rotates to place an open "full" microcartridge 25 in the inhalation chamber 10*c* ready for inhalation delivery through the inhalation port 10*p* (FIG. 1). The rotating holder 75 can hold the open microcartridge 25 during inhalation. Then, the rotating holder 75 rotates the receiver 76 with the empty microcartridge 25 to return the empty microcartridge (the empty status represented by the "X") to a cooperating one of the two return lanes 30*e*, 31*e*. The two adjacent holders 75 can rotate in opposing directions. For example, as shown in FIG. 10, the first holder $75_1$ can rotate clockwise while the second $75_2$ can rotate counterclockwise. The holders 75 can be configured to rotate in the reverse configuration or in the same direction and may be disposed end-to-end rather than side-to-side or even one above the other. Similarly, the holders can hold lesser or greater numbers of microcartridges. In any event, the empty microcartridge 25 can align with the respective cooperating return channel 30*e*, 31*e*, so that the empty container 25 enters the empty channel 30*e*, 31*e*. The rear side of the discharging receiver 76 can be configured to help push the empty container into the lane. The empty return lanes 30*e*, 31*e* can merge back into the same or a different one of the primary travel paths 30, 31.

In some embodiments, the cut lids or remnants 25*t* can be reattached to a used empty cartridge 25 and retained in the inhaler 25. As such, the cut remnant can be directed to travel back to the return lane 30*e*, 30*d* and tape or other material can be applied in situ and used to reconnect the two components together (side by side, under or over a respective empty microcartridge) (not shown). In other embodiments, both the empty microcartridge and the lid 25*t* can be directed into a trash bin in the inhaler 10. To facilitate proper sliding in such an embodiment, a sprocket, gear or other drive mechanism can be used to urge the loaded microcartridges 25 forward along the respective travel path to a dispensing lane 30*d*, 31*d*.

FIG. 6A illustrates that the inhaler 10 may be configured to generally concurrently pick-up a full microcartridge 25 from the dispensing lane 30*d* and release an empty to the return lane 30*e*. FIGS. 6B-6E illustrate another loading cycle that can pick-up from the dispensing lane 30*d* and drop off to the return lane 30*e* that may not occur at the same time using holder 75. In this embodiment, the entry to the return lane 30*e* is disposed closer the entry from the dispensing lane 30*d*. As such, the holder 75 can have periods during each loading cycle where only two of the receiving compartments 75*c* hold a microcartridge 25 (full or empty). As such, a resilient member 125 may reside in the travel path 30*ch* to compress or relax as appropriate to account for the difference in numbers of members 25 in the travel lanes.

Figure 6B:
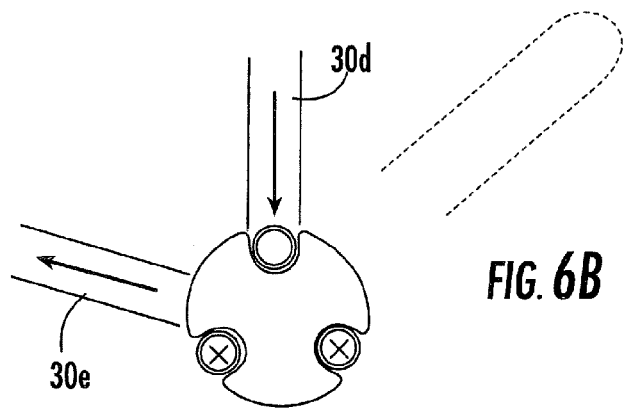
FIGS. 6B-6E are schematic illustrations of a sequence of operations employing an alternate intake and release path relationship according to embodiments of the present invention.
Figure 6C:
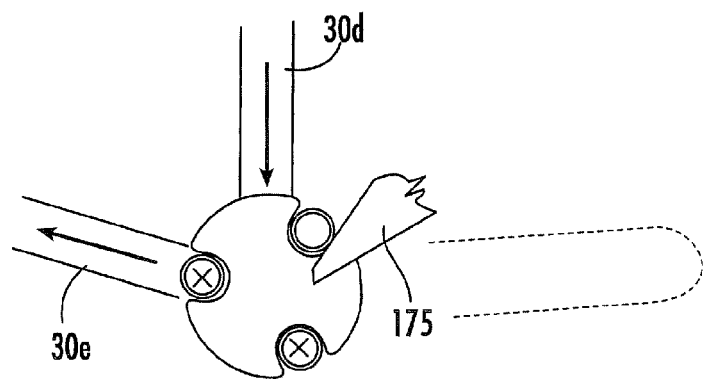
Figure 6D:
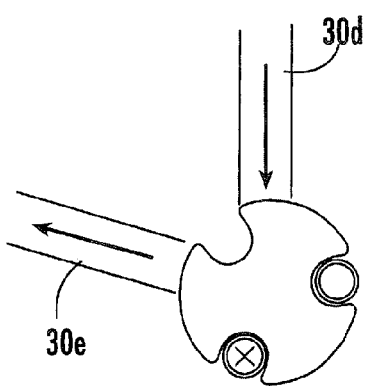
Figure 6E:
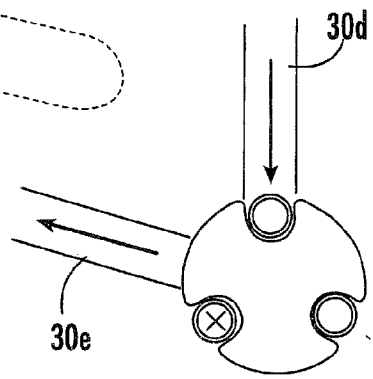

FIG. 6B illustrates the holder 75 with three cartridges 25, one entering from the dispensing lane 30*d*, one in the inhalation chamber 10*c* (now empty or "spent") and another "spent" or empty microcartridge 25 held misaligned with return lane 30*e* before aligning with the return lane 30*e*. This configuration may be the first in an inhalation operation cycle. FIG. 6C illustrates the microcartridge 25 that recently entered the holder 75 in FIG. 6B, is being opened via blade 175, then directed into the inhalation chamber 10*c* as shown in FIGS. 6C-6D. As shown in FIG. 6C, during this translation, the microcartridge holder 75 with the empty microcartridge 25 (represented by the "X") shown in FIG. 6B, now aligns with and exits into return lane 30*e*. As shown in FIG. 6D, the receiving segment 75*c* between the return and dispensing lanes 30*e*, 30*d* is vacant for this portion of the loading cycle. FIG. 6E illustrates the opened microcartridge 25 ready for inhalation delivery and the vacant holder 75*c* approaching the dispensing lane 30*d* for preloading a microcartridge 25 for the next inhalation sequence at the end of the current inhalation sequence. During the configuration shown in FIG. 6B, the travel path 30 can hold one less microcartridge than during the configuration shown in FIG. 6D. As such, the resilient member 125 (FIG. 12) may expand briefly during this portion of the loading cycle then compress during the remaining portions of a respective loading cycle.

In some embodiments, the return lanes 30e, 31e are configured so that the empty microcartridges 25 from the first dispensing path 30d return to the second primary travel path 31 and so that empty microcartridges 25 from the second dispensing path 31d return to the first primary travel path 30. As such, the return lane 30e merges into outer lane 31o and the return lane 31e merges into outer lane 30o of the first primary travel path 30.

Referring again to FIG. 5, the return lanes 30e, 31e are routed adjacent the dispensing lanes 30d, 31d. However, in some embodiments, lane 31e is directed to travel up to lane 30o on the first level 41. As shown in FIG. 5, the return lane 31e include an upwardly ramped floor 39. As shown in FIG. 4A, the top 100 can include a corresponding mating outer ramp segment 139 that decreases in depth in the direction of travel to cause the lane 31e to merge with outer lane 30o. Similarly, the bottom 101 can include a corresponding outer ramp 136 that decreases in height in the direction of travel to cause the lane 30e to merge with 31o.

Figure 9:
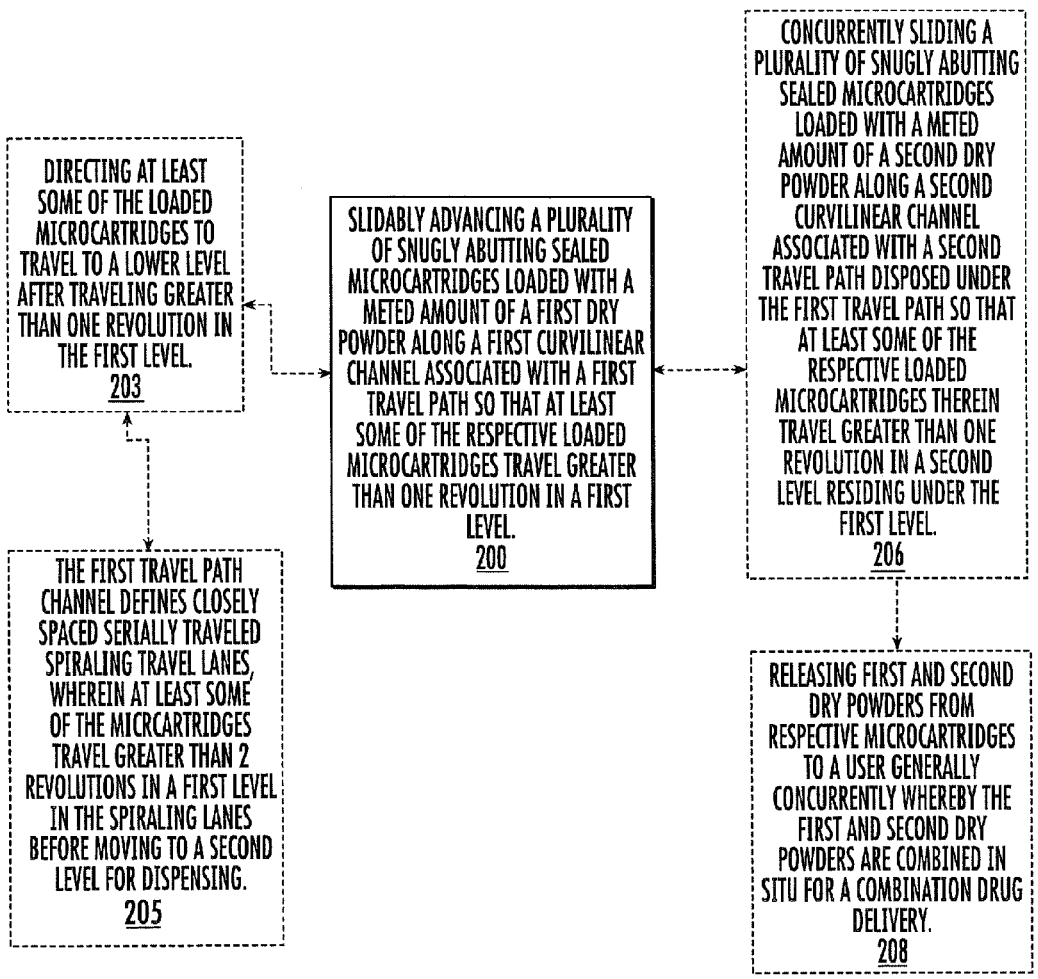
FIG. 9 is a flow chart of operations that can be used to operate an inhaler according to embodiments of the present invention.

FIG. 9 illustrates a method of operating an inhaler. As shown, in operation, a plurality of snugly abutting sealed microcartridges loaded with a meted amount of a first dry powder are slidably advanced (substantially in concert) along a first curvilinear channel associated with a first travel path so that at least some of the respective loaded microcartridges travel greater than one revolution in a first level (block 200).

Optionally, at least some of the loaded microcartridges can be directed to travel for dispensing in an inhalation chamber after traveling greater than one revolution in the first level (block 203). In some embodiments, the first travel path channel defines closely spaced, serially traveled, spiraling travel lanes, and at least some (typically at least a majority) of the microcartridges travel greater than 2 revolutions in a first level in the spiraling lanes before moving to a second level for dispensing (block 205).

In particular embodiments, a plurality of snugly abutting sealed microcartridges loaded with a meted amount of a second dry powder are concurrently slid in concert along a second curvilinear channel associated with a second travel path disposed under the first travel path so that at least some of the respective loaded microcartridges therein travel greater than one revolution in a second level residing under the first level (block 206). In some embodiments, first and second dry powders are substantially concurrently released from respective microcartridges to a user, whereby the first and second dry powders are combined in situ for a combination drug delivery (block 208). The method may also include rotating a loaded sealed microcartridge toward a stationary blade to cut an upper portion thereof open, then vibrating the microcartridge with a predetermined powder-specific vibratory signal.

FIG. 10 illustrates that the inhalation chamber 10*c* can be in communication with a circuit 90*c* that includes a digital signal processor 90, a battery 92 and a vibrator member 95. The signal processor 90 can be configured to control the activation of and/or otherwise communicate with the vibratory member 95 to promote release and/or fluidization of the dry powder during inhalation drug delivery. The signal processor 90 can include modules that provide powder-specific vibratory signals to the powder during inhalation to facilitate a reliable inhalation delivery. Although schematically shown downstream of the opened microcartridges 25$_1$, 25$_2$, in the inhalation chamber 10*c*, the vibrator device 95 may be disposed under, behind (upstream) or above the open microcartridges and inside or outside the inhalation chamber 10*c*. The device 95 can be integrated in the circuit 90*c* and disposed in communication with the cartridges 25$_1$, 25$_2$, in the inhalation chamber 10*c*, directly and/or indirectly. In other embodiments, the vibrator device 95 can reside proximate the inhalation chamber 10*c* (inside or outside thereof) and the remainder of the circuit 90*c* can reside in another portion of the inhaler 10. Traces, leads or wires can be used to provide the electrical connections.

The circuit 90*c* can control certain operations of the inhaler 10. The inhaler 10 can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler 10 can be configured to communicate with a clinician or pharmacy for reorders of medicines and/or patient compliance. The inhaler 10 may also include a second peripheral device communication port (not shown).

In some embodiments, the circuit 90*c* can include computer program code and/or computer applications that communicate additional data to a user (optionally to the display) as noted above and/or communicate with another remote device (the term "remote" including communicating with devices that are local but typically not connected during normal inhalant use).

In some embodiments, the signal processor 90 can be in communication with the vibrator device 95, to generate a priori powder specific excitation signals. The signal processor can be programmed with or in communication with an electronic library of a plurality of desired dry powder excitation signals that can be automatically selected by the processor 90 corresponding to the drug type/drug disposed therein. In this way, customized drug signals can be used to fluidize the dry powder. The circuit 90*c* (FIG. 10) can include electronic memory. The electronic memory can include, but is not limited to, cache, ROM, PROM, EPROM, EEPROM, flash memory, SRAM, and DRAM. The circuit 90*c* can include a computer library module of a priori signals for different drugs or of the drugs held in the inhaler. If the former, the inhaler 10 can select the appropriate one for operation by the inhaler depending on the drug(s) in therein. The library module may be programmed into the memory.

Examples of excitation signals and selection methodology are described in co-pending U.S. Patent Application Publication Nos. 2004-0025877-A1 and 2004-0123864, the contents of which are hereby incorporated by reference as if recited in full herein. For example, the excitation signals can be powder specific and employ a carrier frequency modulated by one or more modulating frequencies (that may be amplitude modulating frequencies) that can facilitate fluidic and reliable flow of the dry powder.

The vibratory signal can include a carrier frequency that may be between about 50 Hz to about 1000 Hz, and typically is between about 100 Hz-1000 Hz. The carrier frequency may be modified by one or more low modulating frequencies (typically between about 10-200 Hz). The frequency of the vibration can be modified to match or correspond to the flow characteristics of the dry powder substance held in the package to attempt to reach a resonant frequency(s) to promote uniform drug dispersion into the body. In some embodiments, a non-linear powder-specific dry powder vibratory energy signal comprises a plurality of selected frequencies that can be generated (corresponding to the particular dry powder(s) being currently dispensed) to output the particular signal corresponding to the dry powder(s) then being dispensed. As used herein, the term "non-linear" means that the vibratory action or signal applied to the dry powder, directly or indirectly, to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. The non-linear vibratory signal input can operate without a fixed single or steady state repeating amplitude at a fixed frequency or cycle. This non-linear vibratory input can be applied to the microcartridge(s) 25 and/or chamber 10c to generate a variable amplitude motion (in either a one, two and/or three-dimensional vibratory motion). The non-linear signal fluidizes the powder in such a way that a powder "flow resonance" is generated allowing active flowable dispensing.

In some embodiments, a signal of combined frequencies can be generated to provide a non-linear signal to improve fluidic flow performance. Selected frequencies can be superimposed to generate a single superposition signal (that may also include weighted amplitudes for certain of the selected frequencies or adjustments of relative amplitudes according to the observed frequency distribution). Thus, the vibratory signal can be a derived non-linear oscillatory or vibratory energy signal used to dispense a particular dry powder. In certain embodiments, the output signal used to activate the transducer or vibrator device 95 may include a plurality of superpositioned modulating frequencies (typically at least three) and a selected carrier frequency. The modulating frequencies can be in the range noted herein (typically between about 10-500 Hz), and, in certain embodiments may include at least three, and typically about four, superpositioned modulating frequencies in the range of between about 10-100 Hz, and more typically, four superpositioned modulating frequencies in the range of between about 10-15 Hz.

The vibrator device 95 can be any suitable vibrator mechanism. The vibrator device 95 can be configured to vibrate the dry powder in the airflow path 10a (indicated by arrows in FIG. 10). In some embodiments, the vibrator device 95 can comprise a transducer that is configured to vibrate the opened cartridge(s) 25 holding the dry powder. Examples of vibrator devices include, but are not limited to, one or more of: (a) ultrasound or other acoustic or sound-based sources (above, below or at audible wavelengths) that can be used to instantaneously apply non-linear pressure signals onto the dry powder; (b) electrical or mechanical vibration of the walls (sidewalls, ceiling and/or floor) of the inhalation flow channel and/or drug cartridge 25, which can include magnetically induced vibrations and/or deflections (which can use electromagnets or permanent field magnets); (c) solenoids, piezoelectrically active portions and the like; and (d) oscillating or pulsed gas (airstreams), which can introduce changes in one or more of volume flow, linear velocity, and/or pressure. Examples of mechanical and/or electromechanical vibratory devices are described in U.S. Pat. Nos. 5,727,607, 5,909,829 and 5,947,169, the contents of which are incorporated by reference as if recited in full herein. In some particular embodiments, the vibrator device 95 includes at least one piezoelectric element, such as a piezoceramic component, and/or a piezoelectric polymer film. Combinations of different vibrating mechanisms can also be used.

In some embodiments, the vibrator device 95 can include a commercially available miniature transducer from Star Micronics (Shizuoka, Japan), having part number QMB-105PX. The transducer can have resonant frequencies in the range of between about 400-600 Hz. However, the inhaler 10 may operate the device 95 "off-resonance" such as between about 1-500 Hz and/or generate a non-linear vibratory signal with a carrier frequency and at least one powder-specific modulating frequency. The non-linear signal can include frequencies between 1-5000 Hz. The vibratory signal output by the device 95 can be powder-specific or customized to the powder(s) being dispensed using a priori signals. If two different dry powders are being concurrently dispensed, the vibratory signal can be delivered via a single transducer (with a common signal) in communication with each microcartridge 25 in the chamber 10c or via separate transducers, each capable of delivering a different vibratory signal to a respective microcartridge 25 in the chamber 10c.

In certain embodiments, the inhaler 10 can include visible indicia (flashing light or display "error" or alert) and/or can be configured to provide audible alerts to warn a user that a microcartridge 25 is misaligned in the inhaler 10 and/or that a dose was properly (and/or improperly) inhaled or released from the inhaler. For example, certain dry powder dose sizes are formulated so that it can be difficult for a user to know whether they have inhaled the medicament (typically the dose is aerosolized and enters the body with little or no taste and/or tactile feel for confirmation). Thus, a sensor (not shown) can be positioned in communication with the flow path 10a in an inhaler and configured to be in communication with a digital signal processor or microcontroller, each held in or on the inhaler. In operation, the sensor can be configured to detect a selected parameter, such as a difference in weight, a density in the exiting aerosol formulation, and the like, to confirm that the dose was released.

Figure 11A:
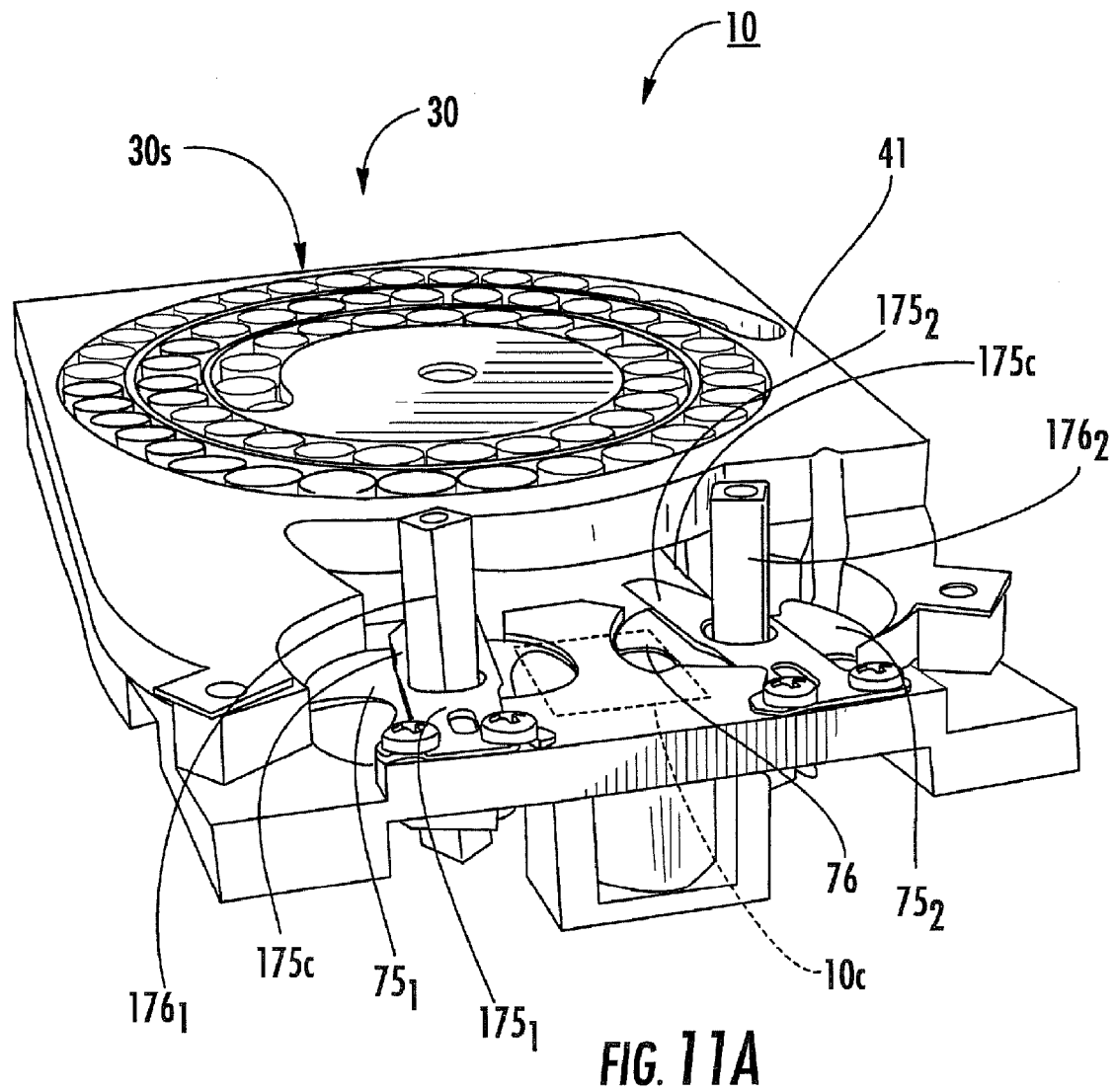
FIG. 11A is an end perspective view of components of an inhaler according to embodiments of the present invention.

Referring to FIG. 11A, the rotating holders $75_1$, $75_2$ are shown with blades $175_1$, $175_2$ thereon. In some embodiments, the blades $175_1$, $175_2$ can be stationary and configured to slice off a top of the microcartridge 25 in the respective holder 175 rotates toward the inhalation chamber 10c. FIG. 11A also illustrates the vibrator device 95 substantially under and between the holders $75_1$, $75_2$ at a medial portion of the inhaler 10. Of course, the blade may optionally translate or one side may translate while the other remains stationary.

Figure 11B:
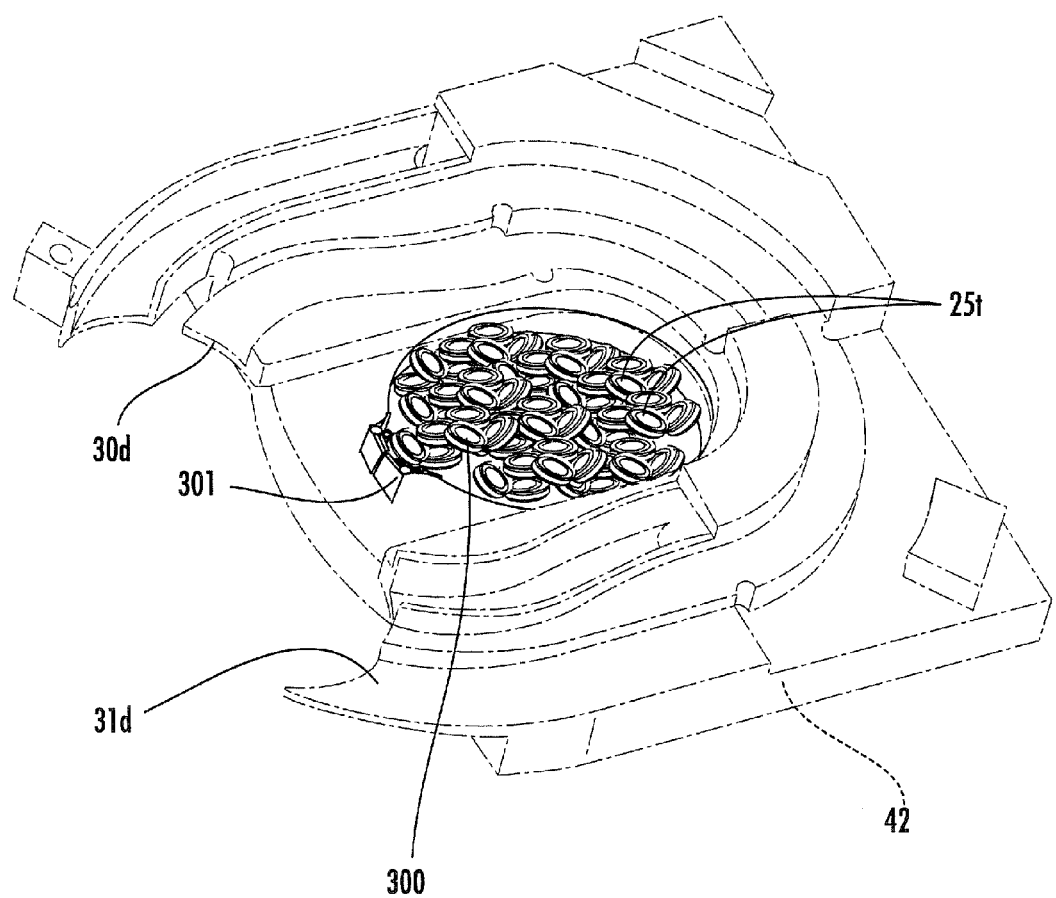
FIG. 11B is a side perspective view schematically illustrating an internal trash bin according to embodiments of the present invention.

In some embodiments, the first holder $175_1$ rotates clockwise and the second holder $175_2$ rotates counterclockwise, each toward the center of the inhaler 10, and the cutting edge 175c is on an outside edge of the respective blade. Each rotating holder $75_1$, $75_2$ can be attached to a post $176_1$, $176_2$ and the blade $175_1$, $175_2$ can extend across and substantially flush with the top surface of the respective holder, with the respective blade 175 being held in a substantially coplanar orientation with the underlying holder 75. In operation, as a holder 75 rotates toward the cutting blade 175, the receiving segment 76 securely holds the microcartridge 25 therein with the top portion of the microcartridge 25 extending above the top surface of the curvilinear receiving segment 76. The holder 75 turns to force the microcartridge 25 against the cutting edge 175c. The cut remnant 25t portion of the microcartridge 25t is directed into a trash bin 300 (FIG. 11B) in the inhaler 10. The cut remnant 25t is prevented from moving into the inhalation chamber 10c by the surface of the blade 175 and may travel rearward into a medial portion of the inhaler into the bin 300 (FIG. 11B) above the top surface of the blade 175 for accumulation. The trash bin 300 may include a gate 301 that is configured to inhibit remnants 25t from leaving the bin, should the inhaler be dropped, shaken, or turned upside down.

It is also noted that the remnant 25t and/or empty microcartridges 25e can be discharged from the inhaler 10 after each deliver or at certain intervals. In some embodiments, a releasable externally accessible cup can be the trash bin 300 which can allow a user to empty as desired (not shown). Optionally, an audio or visual alert can be used to notify a user when to empty the bin 300.

Figure 12:
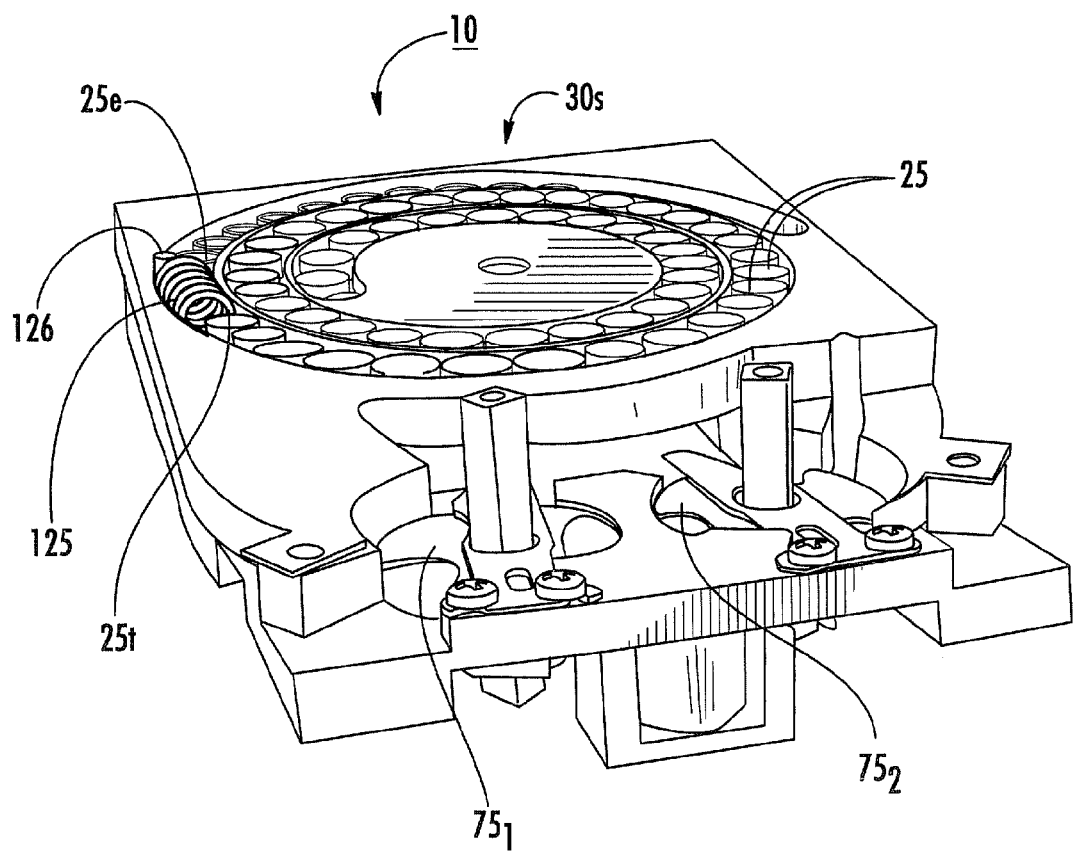
FIG. 12 is an end perspective view of components of an inhaler with a resilient member according to embodiments of the present invention.

FIG. 12 illustrates an example of a queue of microcartridges 25 in the first level 41 in the curvilinear travel path 30s. In this embodiment, a resilient member 125 can be disposed in each of the travel paths 30, 31. The resilient member 125 may comprise a compression spring (as shown), a leaf spring, an elastomeric spring or other type of mechanism configured to advance the "full" microcartridges 25. The resilient member 125 can be configured to impart kinetic and/or potential energy to push the microcartridges 25 upstream thereof along the path. The resilient member 125 typically resides upstream of the return lanes 30e, 31e. In some embodiments, the resilient member 125 can expand and compress a plurality of times during use to compensate for different numbers of microcartridges 25 (or dummies) and/or loading patterns in a travel path 30, 31, such as during each holder loading cycle. For example, at times when there are three microcartridges in the holder 75 (FIGS. 6B, 6C), the member 125 may laterally expand while when there are two in the holder 75 (more in the track) (FIG. 6D), the member 125 can compress. An exemplary length of the compression spring 125, where used, can be between 0.5-2 inches, typically about 1 inch.

As shown, in FIG. 12, the resilient member 125 is typically disposed upstream of the "last" usable dose of medicament in a trailing microcartridge 25t in front of the first "empty" microcartridge 25e. The location of the resilient member will move during operation as the member travels in the channel 30ch (or 31ch). In some embodiments, the initial position of the resilient member 125 is such that at least a rearward portion resides in the return lane 31e, 30e. The resilient member 125 can float in the channel or be attached to structural end members having increased rigidity to maintain the member 125 in the channel.

In addition, dummy members may be placed on either or one end of the resilient member 125 as well. A pin or other retainer member 126 can be used to hold the resilient member in the trailing position. As the return lane 31e becomes full of empty microcartridges 25e as shown in FIG. 12, the rearward ones push forward ones to travel up to the outer lane 30o of the curvilinear path 30s (or if from lane 30e, the empty microcartridges travel down to lane 31o of path 31s). The empty cartridges 25e can travel under a retainer 126 (such as the pin) or other component and push the resilient member 125 forward to force microcartridges upstream thereof to serially travel in the path 30 into the dispensing lane 30d (or 31d). The lower floor can operate in the same or a substantially similar manner.

The movement of the microcartridges 25 in the inhaler 10 can be primarily attributed to the high density loading and/or pushing of the microcartridges 25 along the travel path. The movement can be self-propelled, i.e., the microcartridges 25 or dummies can be substantially free-floating in the respective channel 30ch, 31ch in a snug configuration so that empty containers or dummy members push the upstream full ones. In other embodiments, the floors and/or ceilings of the channels can rotate and/or indexers, gears or other mechanisms can be employed to help to move the microcartridges in the travel lanes 30, 31.

The channel sidewalls, floors or ceilings as well as the microcartridges can be formed of a material that has suitable frictional properties to allow sliding without undue friction. For example, the microcartridges 25 can comprise a polymer body. In addition, the channels 30ch, 31ch can be molded and comprise a polymer and/or material with low friction surfaces, or alternatively, a low friction (smooth/slick) coating can be applied to one or more of the floor, bottom or sides of the channel 30ch, 31ch and/or microcartridges 25.

Figure 13:
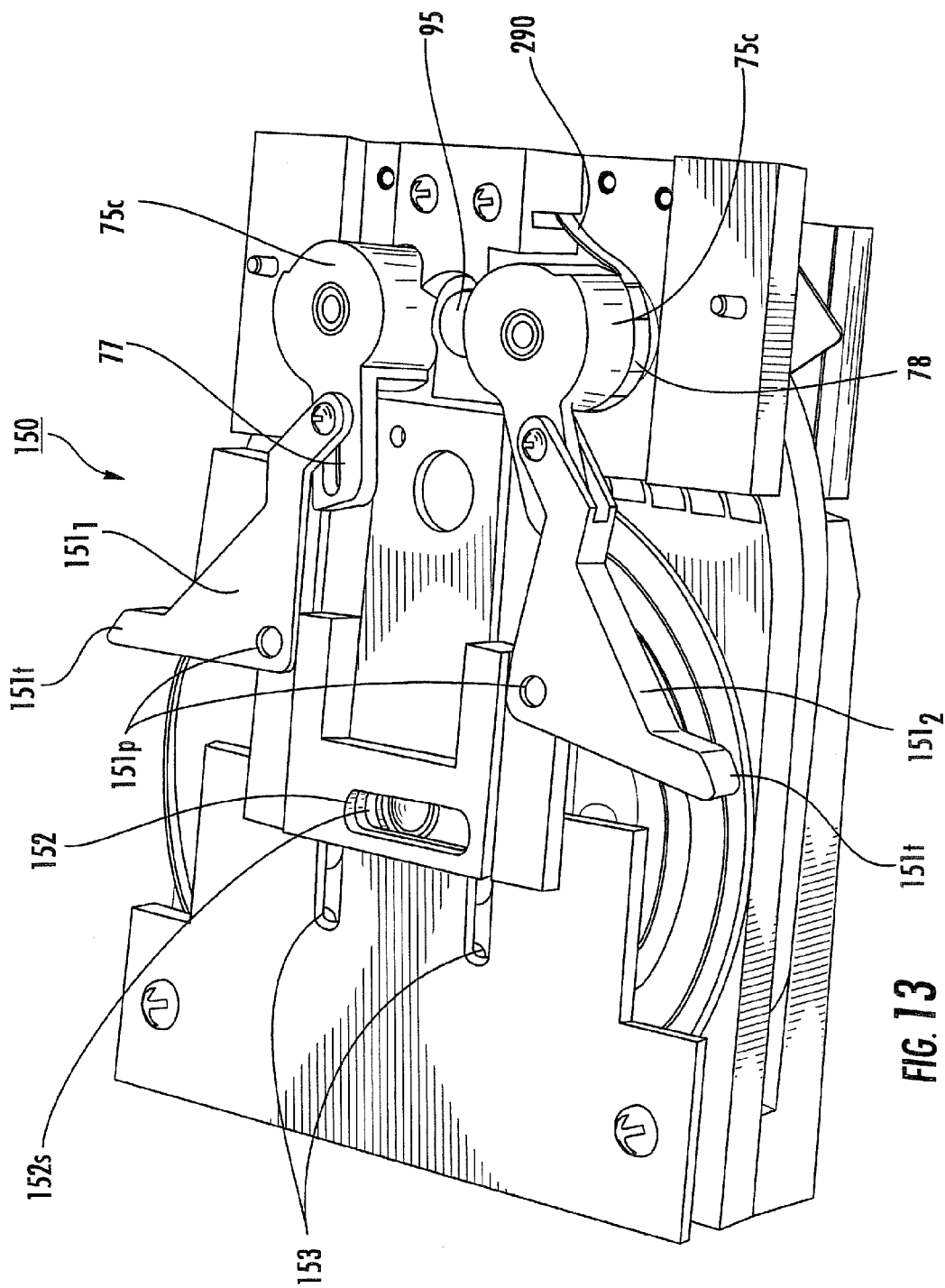
FIG. 13 is a bottom perspective view of a linkage mechanism according to embodiments of the present invention.

FIG. 13 illustrates one embodiment of a linkage mechanism 150 that converts linear movement of a lever-based actuator 15 (FIGS. 1, 15) into rotation of the holders $75_1$, $75_2$ (FIG. 10). As shown, the mechanism 150 includes a center member 152 that slides forward and rearward in slots 153. The slots 153 help keep the member 152 registered in a medial position. The member 152 can also include a lateral slot 152s that engages a pin 15p on the lever 15 (FIG. 15) to translate the center member 152 back and forth. The center member 152 is attached to arms $151_1$, $151_2$ at pivot joints 151p. The forward portion of arms $151_1$, $151_2$ are each attached to a slotted arm 77 that merges into cup 75c. The cup 75 rotates the respective holders 75 with the curved receiving segments 76. During a single stroke, the arms $151_1$, $151_2$ move in the respective slot 77 and rotate the cup 75c about 120 degrees.

Figure 14:
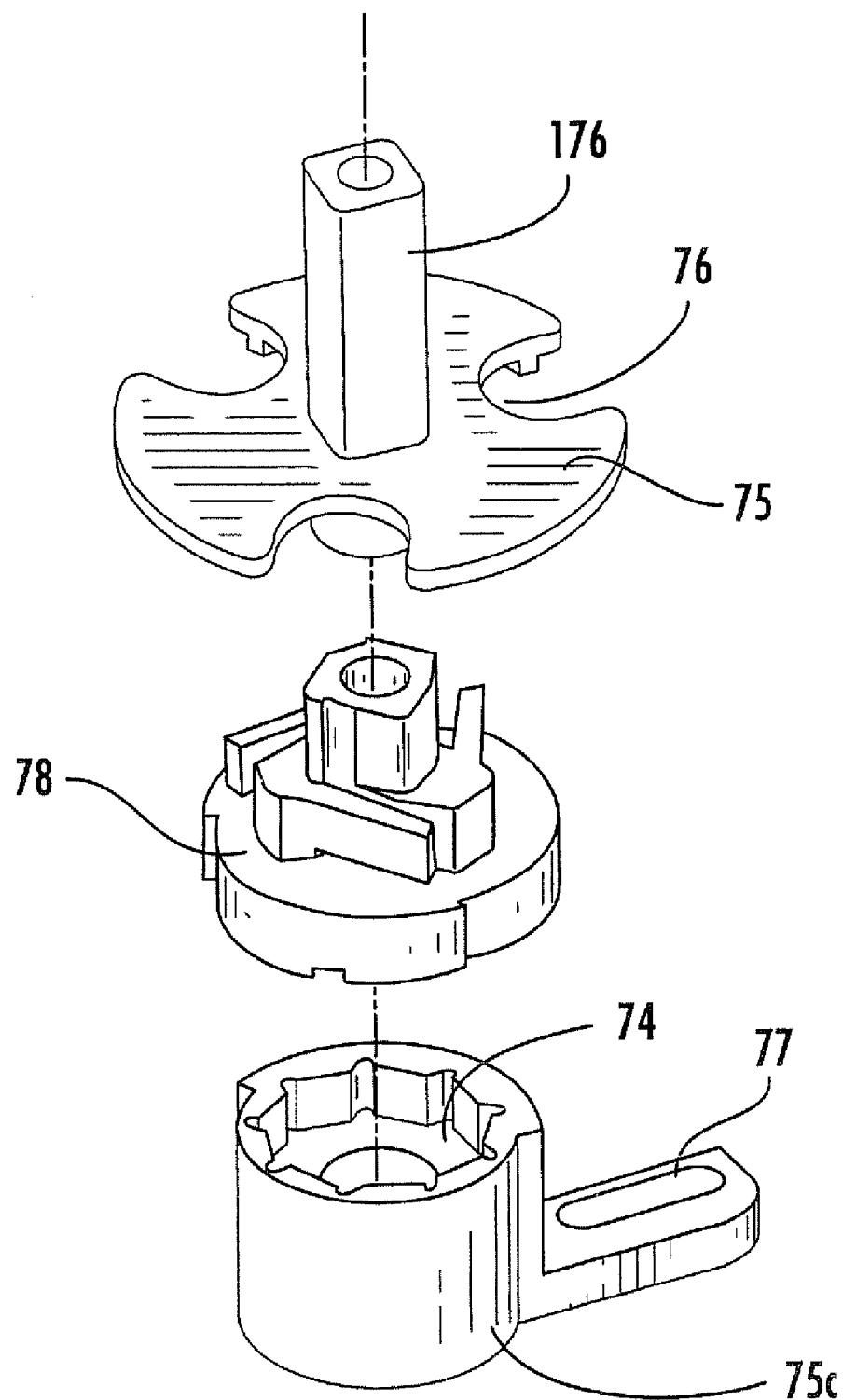
FIG. 14 is an exploded view of a rotating cup assembly according to embodiments of the present invention.

FIG. 14 illustrates an exploded view of a cup assembly above the top of the cup 75c. As shown, the cup 75c includes a receiving cavity 74, which is configured to receive the post 176 and mount the holder 75. The holder 75 can mount to a gripping ratchet 78 that may reside in the cup cavity 74 and turn the holder 75 to allow movement in one direction. The ratchet member 78 is in communication with a pawl 290 (FIG. 13) that is attached to the housing to force/bias the holder 75 to rotate only in the desired direction. The cup cavity 74 may rotate through two positions while the ratchet 78 can rotate through three operative positions to thereby move the holder 75 through three positions. The cup 75c may also include features that inhibit reverse movement.

Figure 15:
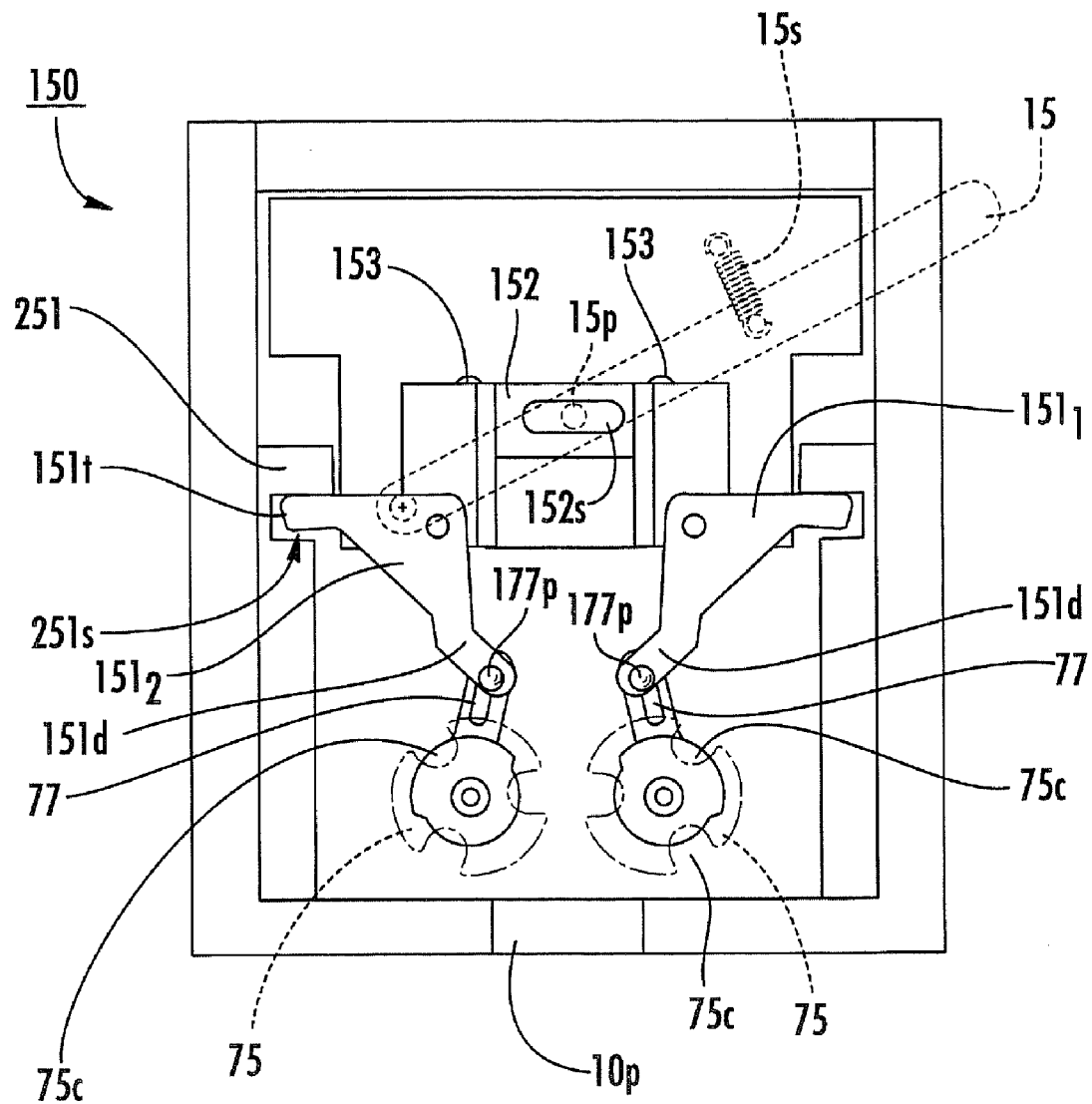
FIGS. 15-17 are sequential views of operational positions of the mechanical linkage shown in FIG. 13 according to embodiments of the present invention.
Figure 16:
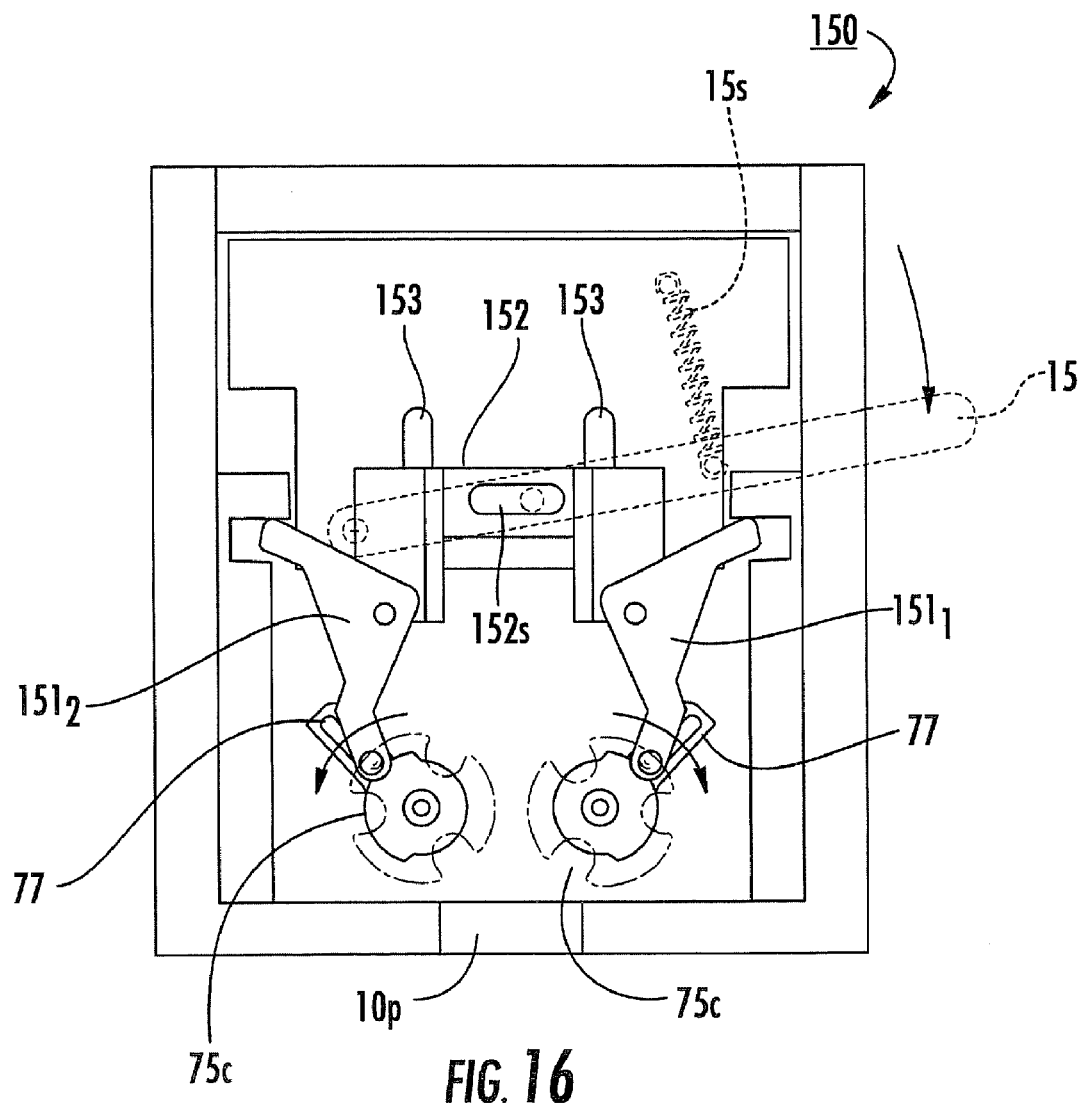
Figure 17:
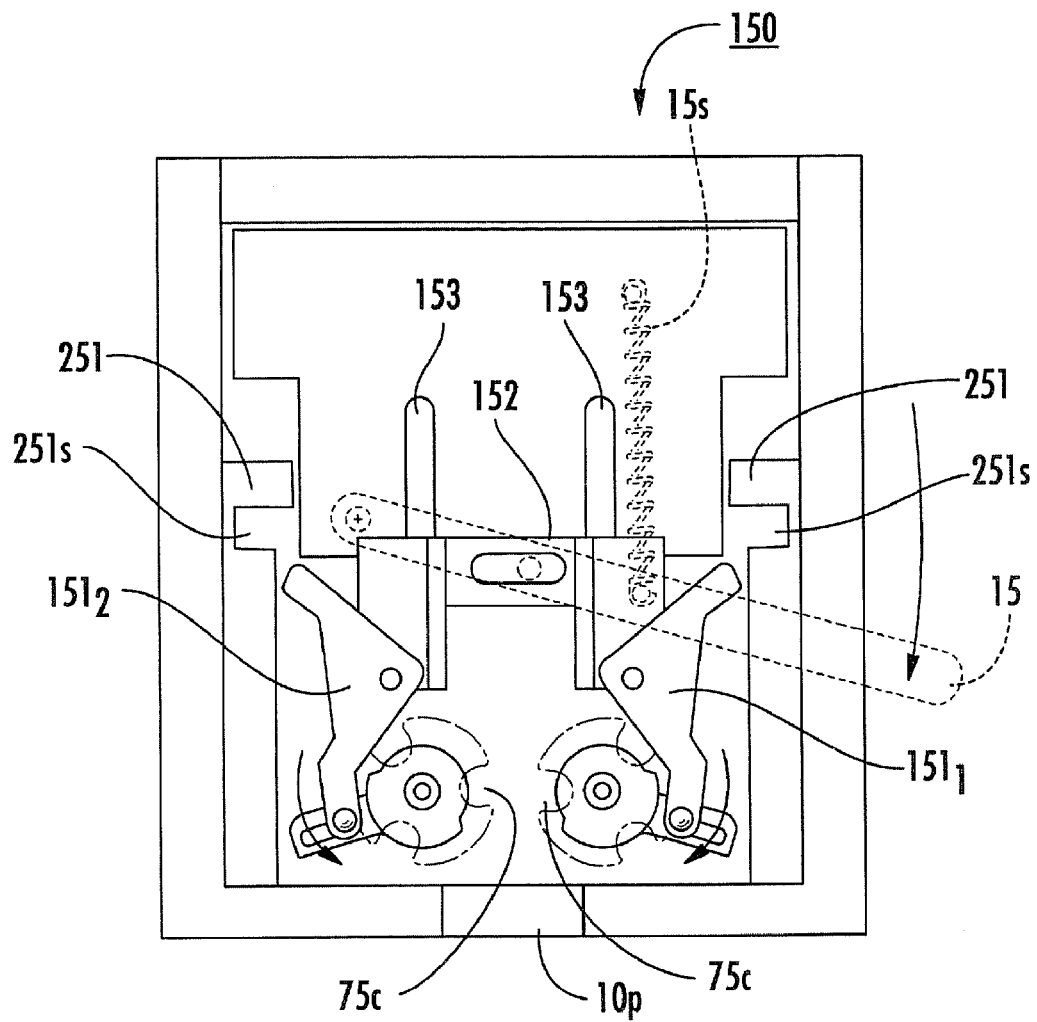

FIGS. 15-17 illustrate that the arms $151_1$, $151_2$ cooperate with and move in and out of a slot 251s in a housing member 251 from a rest to an extended position. In operation, a lever 15 resides in slot 152s which, when moved forward, moves the center member 152 forward. This action causes tip portions 151t of the arms to contact the perimeter wall of the slot 251s, which concurrently pivots both of the arm tips 151t upward and forces the downstream end portions 151d of the respective arms $151_1$, $151_2$ to pivot outward away from each other. As the tips 151d rotate outward, they also move inward along slots 77 toward cups 75c to rotate the cups 75c outward away from each other. The rotation shown is about 120 degrees. Other configurations may be used to provide different rotational operation such as if lesser or greater degrees of rotation are desired.

As shown in FIG. 15, the lever 15 is attached to center member 152 via pin 15p that resides in slot 152s. As the lever 15 moves forward, it causes a sequence of movements of the linkage mechanism 150 that converts the linear movement of the lever 15 into a 120-degree rotation of two holders $75_1$, $75_2$. As shown, a spring 15s can be attached to the lever 15 to bias the lever to return to a start configuration.

Each actuation cycle of the mechanism 150 is configured to move an empty microcartridge 25 to the respective return lane 30e, 31e (FIGS. 6A, 6B), obtain a full microcartridge 25, open a full microcartridge and index the opened full microcartridge into an inhalation position in the inhaler 10 using a single actuation of the lever 15 (back and forth, although rotation is typically only caused by forward motion of the lever). Forward movement of the lever 15 moves the cup 75c about 120 degrees, and a rearward motion places the mechanism 150 in a ready position for the next inhalation dispensing cycle.

Figure 18:
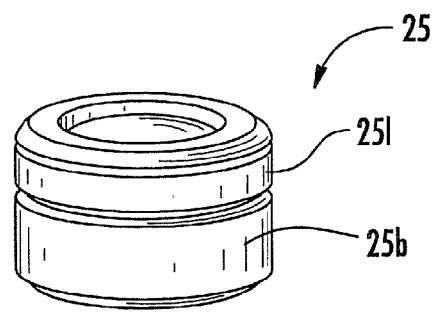
FIG. 18 is a front perspective view of a sealed microcartridge with medicament (such as dry powder) according to embodiments of the present invention.
Figures 19A, 19B:
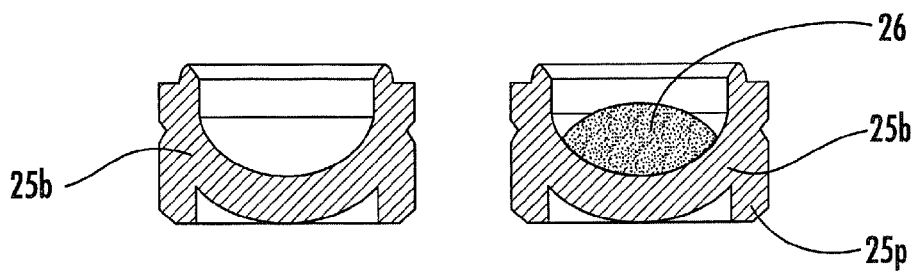
FIGS. 19A-19D are sequential cross-sectional views of exemplary filling and sealing operations of the microcartridge shown in FIG. 18 according to embodiments of the present invention.
Figures 19C, 19D:
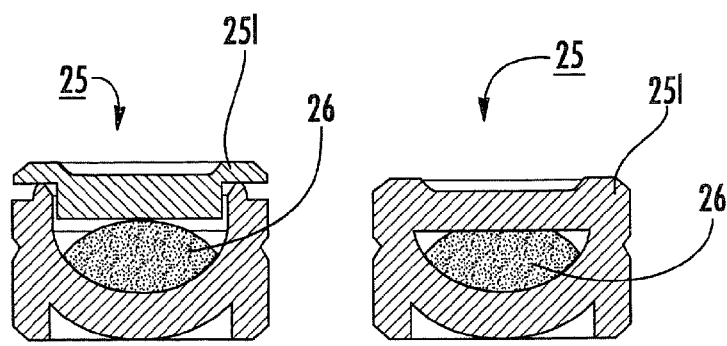
Figure 20A:
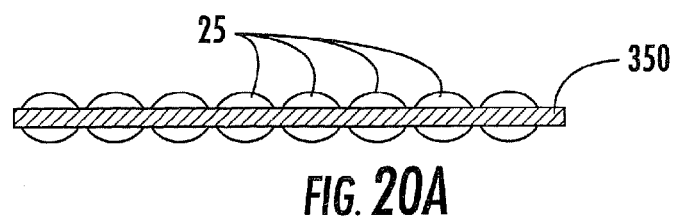
FIG. 20A is a top schematic view of a taped link of microcartridges according to embodiments of the present invention.
Figure 20B:
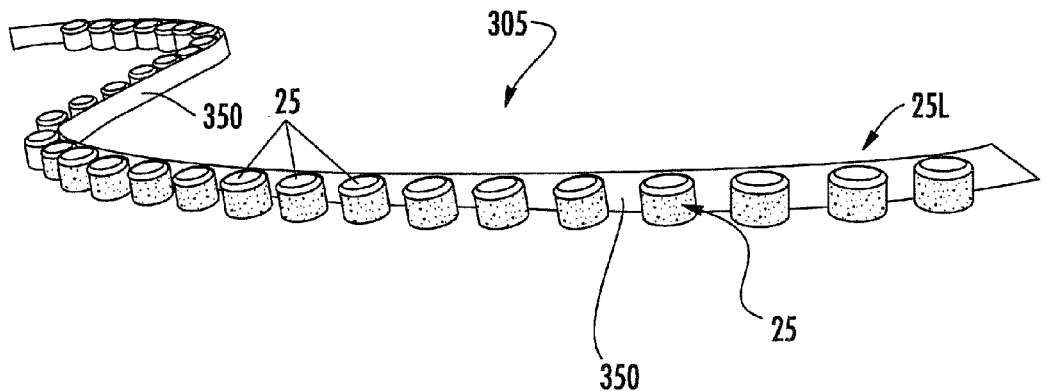
FIG. 20B is a side perspective view of a strip of microcartridges according to some embodiments of the present invention.

FIG. 18 illustrates one embodiment of a sealed microcartridge 25. As shown, the microcartridge includes a body 25b with a holding cavity and a lid 25l. The lid 25l and body 25b can be formed of the same material or different (compatible materials). The lid and/or body of the microcartridge 25 may be molded to have a substantially common thickness sufficient to inhibit moisture and/or oxygen penetration for the desired shelf life. In some embodiments, the microcartridge 25 is formed of an elatomeric material, such as a polymer copolymer or derivatires thereof, and in particular embodiments is formed of a thermoset polymer such as polypropylene (antistatic) and/or polyethylene (antistatic). Examples of suitable material include, but are not limited to, RTP Company Permastat 100, Martex HGL-120-01, and Borealis HJ320MO. The lid 25*l* is attached via any suitable means such as laser welding, ultrasonic welding, friction welding, high frequency welding, brazing, adhesive, or otherwise to affix the lid into position. In some embodiments, the lid 25*l* can be pressed onto the body 25*b* and sealably attached to the body without adhesives. The sealed body may be dipped sprayed or otherwise coated, layered or sealed with another material (metal and/or polymer or other desired material) to enhance the shelf-life or provide additional moisture or oxygen penetration resistance.

The microcartridge 25 can be configured to hold suitable dry powder unit, bolus, or sub-unit doses of medicament therein. In particular embodiments, the microcartridges 25 are configured to deliver meted amounts of a combination of two different medicaments. The sealed microcartridge 25 can be configured so that the water vapor transmission rate can be less than about 1.0 g/100 in$^2$/24 hours, typically less than about 0.6 g/100 in$^2$/24 hours. The microcartridge 25 can have an oxygen transmission rate that is suitable for the dry powder held therein. The microcartridges 25 can be configured with a stable shelf life of between about 1-5 years, typically about 4 years.

The microcartridge 25 can have a volume (prior to filling and sealing) that is less than about 24 mm$^3$, typically less than about 15 mm$^3$. The nominal percent filled at 100% dose, nominal density can be about 40% open to about 75% sealed. The powder bulk density can be about 1 g/cm$^3$ while the power nominal density when filled (for reference) can be about 0.5 g/cm$^3$. The maximum compression of a drug by filling and sealing in the microcartridge 25 can be less than about 5%, typically less than about 2%. The maximum heating of drug during the filling and sealing can be maintained to a desirable level so as not to affect the efficacy of the drug or the formulation.

In some embodiments, a meted amount of dry powder is placed in the open microcartridge body 25*b*, which is then sealed with the rigid lid 25*l* attachment via ultrasonic welding to form the sealed "full" microcartridge. Alternatively, other lid or sealant configurations may be used such as foil, TEDLAR or other suitable materials, including laminates. The microcartridge 25 can be configured to hold about 5 mg total weight of a blended drug. The 5 mg may include lactose or another excipient. During filling, the drug can be compacted in a pre-metered amount and inserted into the microcartridge cavity.

FIGS. 19A-19D illustrate a filling and sealing sequence of microcartridges 25. As shown, the body 25*b* can have a curved (concave) bottom with a perimeter lip 25*p* or may be substantially planar or convex (not shown). In some other embodiments, the microcartridge 25 may have a semi-spherical or dome shaped lid (not shown). In some other embodiments, the entire microcartridge 25 may be substantially spherical and configured to roll (also not shown).

Figure 21:
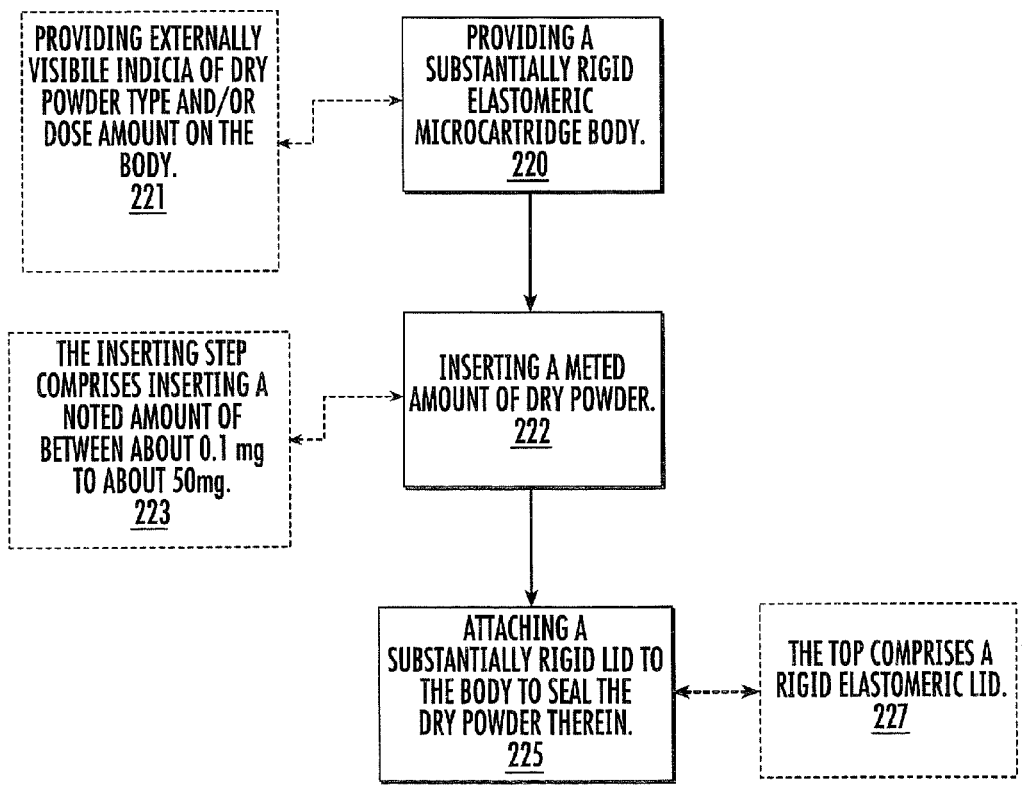
FIG. 21 is a flow chart of operations that can be used to fill microcartridges according to embodiments of the present invention.

FIG. 21 illustrates a method of providing meted dose microcartridges for use in dry powder inhalers. The methods include providing a substantially rigid elastomeric microcartridge body (block 220) and inserting a meted amount of dry powder suitable for inhalation delivery (block 222). Then a substantially rigid top is attached to the body to seal the dry powder therein (block 225). The top can comprise a substantially rigid elastomeric lid (block 227). Optionally, externally visible indicia can be provided on the body to indicate the type of powder and/or dose amount (block 221). The inserting step can include inserting a meted (which may be unit dose) amount of between about 0.1 mg. to about 50 mg of dry powder (block 223).

In embodiments dispensing combination drugs, the microcartridges 25 include externally visual indicia that correspond to a drug therein, to allow manufacturers and automated devices to be able to easily recognize the drug type inserted into the inhaler. This should also facilitate visual confirmation that the correct drugs are in the correct respective channel in the inhaler. The inhaler body can be configured to have the matching indicia on the upper and lower sides of the body so that a "green" cartridge 25 resides in the green portion (channel) and a "white" microcartridge in the white portion (channel). Thus, the channels 30*ch*, 31*ch* and/or respective lid or floors 100, 101 (FIG. 4A) can include corresponding indicia. Thus, the inhalers can be provided in different color combinations corresponding to a dose or drug type held therein. A manufacturing facility can more readily assemble the correct drugs in the correct inhaler and inspect for conformance to the manufacturing lot. Thus, if a low dose of drug one in a microcartridge in a combination inhaler (having a color such as pink) is held in a white inhaler channel intended for a high dose "white" microcartridge, an operator can readily pull the non-compliant inhaler from the assembly line. Thus, the inhaler can be configured with mating components that can be color coded, marked, or otherwise visually marked for different doses and/or different types of drugs. The color-coding can be for the microcartridges 25 and each of the channels 30*ch*, 31*ch* and/or levels 41, 43 and/or other visually accessible inhaler body portions. The color-coding can be a pattern (strip, circles, etc.) or a solid color body or lid.

Also, as discussed above, and shown for example, in FIGS. 1A and 12, when loaded in the inhaler 10, the microcartridges 25 can be discrete bodies that are detached from each other. However, in some embodiments, as shown for example in FIG. 20A, tape 350 can be used to connect the microcartridges 25. The tape 350 can help load the cartridges 25 in a desired alignment in the curvilinear channel 30*ch*, 31*ch*. The tape 350 may be single sided tape that can be removed once the containers 25 are held in the channel in the desired loading density. The tape 350 may be color coded to the particular drug/dose as well to facilitate correct loading of the inhaler 10. The channels can be configured to retain the microcartridges 25 from vertical movement, so that the tape or other substrate can be pulled off leaving the microcartridges 25 in position. That is, a "string" or link of attached microcartridges can be pulled into the spiral portion of the travel path, then the tape can be removed. In other embodiments, the tape 350 can remain and the bodies 25 separated from the tape 350 as they are rotated in the holder 75 or in advance of movement into the holder 75. As shown in FIG. 20B, the microcartridges 25 can be attached on a side rather than a top or bottom and some space may remain between neighboring microcartridges 25. Of course, the bodies 25 may alternatively be arranged to abut as well. For each of the embodiments shown in FIGS. 20A and 20B, the tape or substrate 350 can remain on the microcartridges 25 and be used to roll or pull the microcartridges 25 along a portion, or substantially all, of the travel path to the inhalation chamber 10*c*.

While the present invention is illustrated, for example, with reference to particular divisions of programs, functions and memories, the present invention should not be construed as limited to such logical divisions. Thus, the present invention(s) should not be construed as limited to the configurations shown and described, as the invention(s) is intended to encompass any configuration capable of carrying out the operations described herein.

Certain embodiments may be particularly suitable for dispensing medication to diabetic patients, cystic fibrosis patients and/or patients having diseases or impairments where variable bolus medicaments are desired. Other embodiments may be particularly suitable for dispensing narcotics, hormones and/or infertility treatments.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A dry powder inhaler, comprising:
a first generally planar spiral travel path in an inhaler body, wherein the first spiral travel path has a plurality of adjacent curvilinear channels forming lanes with respective laterally spaced apart upstanding sidewalls, including an inner lane and an outer lane; and
a plurality of discrete microcartridges with substantially rigid bodies disposed in the first travel path, the microcartridges each having a bottom, a top and an outer wall extending therebetween enclosing a sealed cavity, each cavity comprising a pre-metered amount of dry powder, the microcartridges being configured to slidably advance along the first travel path toward an inhalation chamber that merges into an inhalation output port, wherein, in operation, at least one microcartridge is held in the inhalation chamber to release the dry powder therein during inhalation, wherein the microcartridges are oriented in the channels so that their outer walls reside proximate respective laterally spaced apart channel sidewalls and the bottom faces a floor of the channel, and wherein outer walls of neighboring microcartridge bodies are in abutting contact as they slidably advance to the inhalation chamber.

2. An inhaler according to claim 1, further comprising:
a second generally planar spiral travel path, wherein the second spiral travel path has a plurality of curvilinear channels forming lanes with upstanding sidewalls, including an inner lane and an outer lane; and
a second plurality of discrete sealed microcartridges, each comprising a pre-metered amount of dry powder, disposed in the second travel path, the microcartridges being configured to slidably advance along the second travel path toward the inhalation chamber that merges into the inhalation output port.

3. An inhaler according to claim 2, wherein the discrete sealed bodies travel in single file, captured between the sidewalls, and substantially all microcartridges comprising dry powder snugly abut neighboring adjacent microcartridges, and wherein the single file microcartridges are configured to slidably push microcartridges downstream thereof in a dispensing direction toward the inner lane that merges into a dispensing lane.

4. An inhaler according to claim 3, wherein, in operation, two microcartridges are held in the inhalation chamber, one from each of the first and second travel paths, and each is serially or concurrently cut open by at least one cutting member to release the respective dry powder therein during inhalation.

5. An inhaler according to claim 4, further comprising a trash receptacle that captures cut portions of the microcartridges.

6. An inhaler according to claim 1, further comprising at least one vibration device in communication with the inhalation chamber.

7. An inhaler according to claim 1, wherein the first spiral travel path includes at least one medial lane with upwardly extending sidewalls disposed between the inner and outer lanes.

8. An inhaler according to claim 7, wherein at least some of the microcartridges in the first and second spiral paths are configured to snugly abut each other and move substantially in concert about at least a major portion of the respective travel paths to push microcartridges forward along a dispensing lane.

9. A dry powder inhaler, comprising:
a first generally planar spiral travel path in an inhaler body, wherein the first spiral travel path has a plurality of adjacent curvilinear channels forming lanes with upstanding sidewalls, including an inner lane and an outer lane;
a plurality of discrete sealed microcartridges with substantially rigid bodies disposed in the first travel path, each comprising a pre-metered amount of dry powder, the microcartridges being configured to slidably advance along the first travel path toward an inhalation chamber that merges into an inhalation output port, wherein, in operation, at least one microcartridge is held in the inhalation chamber to release the dry powder therein during inhalation; and
first and second rotating microcartridge holders, one disposed in cooperating communication with the first travel path and the other disposed in cooperating communication with the second travel path, wherein the holders are configured to receive a respective sealed microcartridge, rotate to force the microcartridge against a cutting blade in cooperating communication with the respective holder to open the microcartridge, then hold the respective opened microcartridge in the inhalation chamber during inhalation.

10. An inhaler according to claim 9, wherein the first rotating microcartridge holder rotates clockwise and the second microcartridge holder rotates counterclockwise.

11. An inhaler according to claim 10, wherein the microcartridge holders include a plurality of circumferentially spaced apart, substantially arcuately shaped receiving chambers, wherein, in operation, the holders are configured to concurrently hold a plurality of microcartridges, including at least one with dry powder in each holder in the inhalation chamber for concurrent combination drug delivery.

12. An inhaler according to claim 11, wherein the microcartridges extend a distance above the respective holder when held therein, and wherein the inhaler further comprises a static first cutting blade extending above the first holder and a second static cutting blade above the second holder, each blade at a height sufficient to cut an upper portion off a microcartridge as the respective holder rotates to force a sealed microcartridge against the cutting blade.

13. An inhaler according to claim 9, further comprising a dispensing lane that extends between the inner lane of the first spiral travel path and the first rotating holder in the inhalation chamber.

14. An inhaler according to claim 9, wherein the first spiral travel path is on a first level and the second spiral travel path is on a third level thereunder, and wherein the first and second rotating holders and the inhalation chamber are disposed on a second level between the first and third levels.

15. An inhaler according to claim 9, wherein, in operation, an empty microcartridge from the first microcartridge holder is automatically directed to the outer lane of the second spiral travel path and an empty microcartridge from the second microcartridge holder is automatically directed to the outer lane of the first spiral travel path.

16. An inhaler according to claim 9, further comprising an actuator in communication with a linkage mechanism that is attached to the first and second holders, wherein the linkage mechanism converts linear motion to rotational motion of the first and second holders to position opened microcartridges in the inhalation chamber ready for inhalation.

17. A dry powder inhaler, comprising:
    first and second curvilinear travel paths in an inhaler body, each curvilinear travel path comprising a plurality of curvilinear side-by-side lanes on a substantially common plane, the curvilinear travel paths comprising a respective dispensing lane that leads to a common inhalation delivery chamber in fluid communication with an inhalation port; and
    a plurality of discrete microcartridges, each comprising a bottom, a top and an outer wall extending therebetween enclosing a sealed cavity with a meted amount of dry powder, wherein at least some of the microcartridge outer walls disposed in each of the first and second travel paths snugly abut neighboring microcartridge outerwalls, and wherein the microcartridges slidably advance along the respective travel paths with the bottom facing a floor of the respective dispensing lane.

18. A dry powder inhaler according to claim 17, wherein at least a major portion of the first travel path resides above the second travel path.

19. A dry powder inhaler according to claim 17, wherein at least a major portion of the first and second travel paths reside side-by-side and substantially coplanar.

20. An inhaler according to claim 17, wherein the curvilinear travel paths comprise spiraling lanes that are serially traveled by a respective microcartridge in a dispensing direction, and wherein each curvilinear travel path can hold about 60 microcartridges.

21. An inhaler according to claim 17, wherein the first travel path has a dispensing lane that directs microcartridges from an inner lane of the first travel path to the first microcartridge holder, and wherein the first travel path has a return lane that directs empty microcartridges to travel to an outer lane in the second curvilinear travel path.

22. An inhaler according to claim 17, further comprising a trash receptacle in communication with the microcartridge holders for automatically capturing remnants of used microcartridges.

23. A dry powder inhaler, comprising:
    first and second curvilinear travel paths in an inhaler body, each curvilinear travel path comprising a plurality of curvilinear side-by-side lanes on a substantially common plane, the curvilinear travel paths comprising a respective dispensing lane that leads to a common inhalation delivery chamber in fluid communication with an inhalation port;
    a plurality of discrete microcartridges, each comprising a meted amount of dry powder, wherein at least some of the microcartridges disposed in each of the first and second travel paths snugly abut neighboring microcartridges, and wherein the microcartridges slidably advance along the respective travel paths to the respective dispensing lane;
    rotatable first and second spaced apart microcartridge holders in cooperating communication with a respective one of the dispensing lanes of the first and second travel paths; and
    first and second cutting blades, one in communication with a respective one of the first and second holders, wherein as a respective loaded sealed microcartridge enters the respective microcartridge holder from the respective dispensing lane, the respective holder rotates to force the loaded sealed microcartridge against the cutting blade to cut the microcartridge open and expose the dry powder therein, then position the opened loaded microcartridge in the inhalation chamber; and
    at least one vibration device in communication with the inhalation delivery chamber, wherein at least one desired vibratory signal is applied to the dry powder during inhalation.

24. An inhaler according to claim 23, wherein one of the first and second microcartridge holders rotates in a clockwise direction and the other rotates in a counterclockwise direction.

* * * * *

UNITED STATES PATENT AND TRADEMARK OFFICE
CERTIFICATE OF CORRECTION

| | | |
|---|---|---|
| PATENT NO. | : 7,987,845 B2 | Page 1 of 1 |
| APPLICATION NO. | : 11/625855 | |
| DATED | : August 2, 2011 | |
| INVENTOR(S) | : King et al. | |

It is certified that error appears in the above-identified patent and that said Letters Patent is hereby corrected as shown below:

Column 20, Line 38: Please correct "1A and 12" to read -- 11A and 12 --

Signed and Sealed this
Twenty-second Day of November, 2011

David J. Kappos
*Director of the United States Patent and Trademark Office*

UNITED STATES PATENT AND TRADEMARK OFFICE
CERTIFICATE OF CORRECTION

PATENT NO.        : 7,987,845 B2                                   Page 1 of 1
APPLICATION NO.   : 11/625855
DATED             : August 2, 2011
INVENTOR(S)       : King et al.

It is certified that error appears in the above-identified patent and that said Letters Patent is hereby corrected as shown below:

<u>In the Claims:</u>
Column 22, Claim 9, Line 49: Correct "the second travel path,"
to read -- a second travel path, --

Signed and Sealed this
Twenty-fourth Day of June, 2014

Michelle K. Lee
*Deputy Director of the United States Patent and Trademark Office*